(12) United States Patent
Lechmann et al.

(10) Patent No.: US 8,449,576 B2
(45) Date of Patent: May 28, 2013

(54) DYNAMIC FIXATION SYSTEM

(75) Inventors: Beat Lechmann, Grenchen (CH);
Volker Engelmann, Muenchenstein (CH); Markus Kraft, Frenkendorf (CH); Michael Gabl, Telfs (AT); Andreas Baeriswyl, Bueren an der Aare (CH)

(73) Assignee: DePuy Synthes Products, LLC, Raynham, MA (US)

( * ) Notice: Subject to any disclaimer, the term of this patent is extended or adjusted under 35 U.S.C. 154(b) by 583 days.

(21) Appl. No.: 12/305,272

(22) PCT Filed: Jun. 28, 2007

(86) PCT No.: PCT/US2007/072366
§ 371 (c)(1),
(2), (4) Date: May 28, 2009

(87) PCT Pub. No.: WO2008/003047
PCT Pub. Date: Jan. 3, 2008

(65) Prior Publication Data
US 2010/0069964 A1      Mar. 18, 2010

Related U.S. Application Data

(60) Provisional application No. 60/817,474, filed on Jun. 28, 2006.

(51) Int. Cl.
*A61B 17/70* (2006.01)
(52) U.S. Cl.
USPC ........... 606/257; 606/254; 606/256; 606/259; 606/262
(58) Field of Classification Search
USPC ................................ 606/246–279
See application file for complete search history.

(56) References Cited

U.S. PATENT DOCUMENTS

| 4,041,939 A | 8/1977 | Hall |
| 4,369,769 A | 1/1983 | Edwards |

(Continued)

FOREIGN PATENT DOCUMENTS

| DE | 2821678 | 11/1979 |
| DE | 4109941 | 10/1992 |

(Continued)

OTHER PUBLICATIONS

International Search Report, completed Dec. 14, 2007 for PCT International Application No. PCT/US2007/072366, filed Jun. 28, 2007.

(Continued)

*Primary Examiner* — Eduardo C Robert
*Assistant Examiner* — Nicholas Plionis
(74) *Attorney, Agent, or Firm* — Stradley Ronon Stevens & Young, LLP

(57) ABSTRACT

The present invention is directed to a dynamic fixation system for engaging, via bone fixation elements, one or more parts of a patient's body. Preferably, the dynamic fixation system is used to engage one or more vertebrae for stabilizing the attached vertebrae with respect to one another while still permitting the vertebrae to move with respect to one another. The dynamic fixation system may include a first rod having first and second ends, a second rod having first and second ends, and a damping component and/or a damping mechanism for interconnecting the first and second rods. In one embodiment, the damping component is injection molded in-between the one of the ends of the first rod and one of the ends of the second rod so that the first and second rods are prevented from separating with respect to one another but are still permitted to move with respect to one another.

13 Claims, 23 Drawing Sheets

U.S. PATENT DOCUMENTS

| | | | |
|---|---|---|---|
| 4,369,772 A * | 1/1983 | Miller | 606/92 |
| 4,448,191 A | 5/1984 | Rodnyansky et al. | |
| 4,743,260 A | 5/1988 | Burton | |
| 4,932,975 A | 6/1990 | Main et al. | |
| 5,002,576 A | 3/1991 | Fuhrmann et al. | |
| 5,011,497 A | 4/1991 | Persson et al. | |
| 5,084,048 A | 1/1992 | Jacob et al. | |
| 5,180,393 A | 1/1993 | Commarmond | |
| 5,282,863 A | 2/1994 | Burton | |
| 5,375,823 A | 12/1994 | Navas | |
| 5,413,576 A | 5/1995 | Rivard | |
| 5,415,661 A | 5/1995 | Holmes | |
| 5,423,816 A | 6/1995 | Lin | |
| 5,480,401 A | 1/1996 | Navas | |
| 5,488,761 A | 2/1996 | Leone | |
| 5,536,268 A | 7/1996 | Griss | |
| 5,540,688 A | 7/1996 | Navas | |
| 5,562,737 A | 10/1996 | Graf | |
| 5,573,520 A | 11/1996 | Schwartz et al. | |
| 5,649,925 A | 7/1997 | Barbera Alacreu | |
| 5,658,286 A | 8/1997 | Sava | |
| 5,662,651 A | 9/1997 | Tornier et al. | |
| 5,672,175 A | 9/1997 | Martin | |
| 5,681,311 A | 10/1997 | Foley et al. | |
| 5,713,900 A | 2/1998 | Benzel et al. | |
| 5,725,582 A | 3/1998 | Bevan et al. | |
| 5,733,284 A | 3/1998 | Martin | |
| 5,814,046 A | 9/1998 | Hopf | |
| RE36,221 E | 6/1999 | Breard et al. | |
| 6,053,922 A | 4/2000 | Krause et al. | |
| 6,241,730 B1 | 6/2001 | Alby | |
| 6,267,764 B1 | 7/2001 | Elberg | |
| 6,290,700 B1 | 9/2001 | Schmotzer | |
| 6,293,949 B1 | 9/2001 | Justis et al. | |
| 6,296,644 B1 | 10/2001 | Saurat et al. | |
| 6,337,142 B2 | 1/2002 | Harder et al. | |
| 6,402,750 B1 | 6/2002 | Atkinson et al. | |
| 6,440,169 B1 | 8/2002 | Elberg et al. | |
| 6,447,518 B1 | 9/2002 | Krause et al. | |
| 6,488,682 B2 | 12/2002 | Kikuchi et al. | |
| 6,554,831 B1 | 4/2003 | Rivard et al. | |
| 6,585,769 B1 | 7/2003 | Muhanna et al. | |
| 6,607,558 B2 * | 8/2003 | Kuras | 623/17.16 |
| 6,626,905 B1 | 9/2003 | Schmiel et al. | |
| 6,626,909 B2 | 9/2003 | Chin | |
| 6,645,207 B2 | 11/2003 | Dixon et al. | |
| 6,652,585 B2 | 11/2003 | Lange | |
| 6,682,533 B1 | 1/2004 | Dinsdale et al. | |
| 6,706,044 B2 | 3/2004 | Kuslich et al. | |
| 6,749,614 B2 | 6/2004 | Teitelbaum et al. | |
| 6,783,527 B2 | 8/2004 | Drewry et al. | |
| 6,835,205 B2 | 12/2004 | Atkinson et al. | |
| 6,884,241 B2 | 4/2005 | Bertranou et al. | |
| 6,966,910 B2 | 11/2005 | Ritland | |
| 6,986,771 B2 | 1/2006 | Paul et al. | |
| 6,989,011 B2 | 1/2006 | Paul et al. | |
| 7,083,621 B2 | 8/2006 | Shaolian et al. | |
| 7,094,237 B2 | 8/2006 | Gradel et al. | |
| 7,097,648 B1 | 8/2006 | Globerman et al. | |
| 7,125,410 B2 | 10/2006 | Freudiger | |
| 7,229,441 B2 | 6/2007 | Trieu et al. | |
| 7,335,200 B2 | 2/2008 | Carli | |
| 2002/0035366 A1 | 3/2002 | Walder et al. | |
| 2002/0055740 A1 | 5/2002 | Lieberman | |
| 2002/0082600 A1 | 6/2002 | Shaolian et al. | |
| 2002/0087159 A1 | 7/2002 | Thomas | |
| 2002/0123750 A1 | 9/2002 | Eisermann et al. | |
| 2003/0032958 A1 | 2/2003 | Soubeiran | |
| 2003/0040746 A1 | 2/2003 | Mitchell et al. | |
| 2003/0088251 A1 | 5/2003 | Braun et al. | |
| 2003/0109880 A1 | 6/2003 | Shirado et al. | |
| 2003/0171749 A1 | 9/2003 | Le Couedic et al. | |
| 2003/0195514 A1 | 10/2003 | Trieu et al. | |
| 2003/0220643 A1 | 11/2003 | Ferree | |
| 2004/0049189 A1 | 3/2004 | Le Couedic et al. | |
| 2004/0049190 A1 | 3/2004 | Biedermann et al. | |
| 2004/0143264 A1 | 7/2004 | McAfee | |
| 2004/0147928 A1 | 7/2004 | Landry et al. | |
| 2004/0215191 A1 | 10/2004 | Kitchen | |
| 2004/0215193 A1 | 10/2004 | Shaolian et al. | |
| 2004/0236329 A1 | 11/2004 | Panjabi | |
| 2004/0267260 A1 | 12/2004 | Mack et al. | |
| 2005/0033295 A1 | 2/2005 | Wisnewski | |
| 2005/0049708 A1 | 3/2005 | Atkinson et al. | |
| 2005/0065516 A1 | 3/2005 | Jahng | |
| 2005/0085815 A1 | 4/2005 | Harms et al. | |
| 2005/0090822 A1 | 4/2005 | DiPoto | |
| 2005/0101957 A1 | 5/2005 | Buskirk et al. | |
| 2005/0113927 A1 | 5/2005 | Malek | |
| 2005/0131408 A1 * | 6/2005 | Sicvol et al. | 606/61 |
| 2005/0154390 A1 | 7/2005 | Biedermann et al. | |
| 2005/0165396 A1 | 7/2005 | Fortin et al. | |
| 2005/0171539 A1 | 8/2005 | Braun et al. | |
| 2005/0171540 A1 | 8/2005 | Lim et al. | |
| 2005/0171543 A1 | 8/2005 | Timm et al. | |
| 2005/0177156 A1 | 8/2005 | Timm et al. | |
| 2005/0177157 A1 | 8/2005 | Jahng | |
| 2005/0182401 A1 | 8/2005 | Timm et al. | |
| 2005/0182409 A1 | 8/2005 | Callahan et al. | |
| 2005/0203511 A1 | 9/2005 | Wilson-MacDonald et al. | |
| 2005/0203513 A1 | 9/2005 | Jahng et al. | |
| 2005/0203517 A1 | 9/2005 | Jahng et al. | |
| 2005/0203519 A1 | 9/2005 | Harms et al. | |
| 2005/0216005 A1 * | 9/2005 | Howland | 606/61 |
| 2005/0222569 A1 | 10/2005 | Panjabi | |
| 2005/0228381 A1 | 10/2005 | Kirschman | |
| 2005/0245930 A1 | 11/2005 | Timm et al. | |
| 2005/0261682 A1 | 11/2005 | Ferree | |
| 2005/0261685 A1 * | 11/2005 | Fortin et al. | 606/61 |
| 2005/0261686 A1 | 11/2005 | Paul | |
| 2005/0277922 A1 | 12/2005 | Trieu et al. | |
| 2005/0288670 A1 | 12/2005 | Panjabi et al. | |
| 2005/0288672 A1 | 12/2005 | Ferree | |
| 2006/0015100 A1 | 1/2006 | Panjabi et al. | |
| 2006/0036240 A1 | 2/2006 | Colleran et al. | |
| 2006/0084982 A1 | 4/2006 | Kim | |
| 2006/0111715 A1 | 5/2006 | Jackson | |
| 2006/0129147 A1 | 6/2006 | Biedermann et al. | |
| 2006/0142758 A1 | 6/2006 | Petit | |
| 2006/0142760 A1 | 6/2006 | McDonnell | |
| 2006/0149238 A1 | 7/2006 | Sherman et al. | |
| 2006/0189983 A1 | 8/2006 | Fallin et al. | |
| 2006/0189984 A1 | 8/2006 | Fallin et al. | |
| 2006/0212033 A1 | 9/2006 | Rothman et al. | |
| 2006/0229612 A1 | 10/2006 | Rothman et al. | |
| 2006/0240533 A1 | 10/2006 | Sengupta et al. | |
| 2006/0260483 A1 | 11/2006 | Hartmann et al. | |
| 2006/0264940 A1 | 11/2006 | Hartmann | |
| 2006/0293657 A1 | 12/2006 | Hartmann | |
| 2007/0016193 A1 | 1/2007 | Ritland | |
| 2007/0073293 A1 | 3/2007 | Martz et al. | |
| 2007/0112428 A1 * | 5/2007 | Lancial | 623/17.12 |
| 2007/0123865 A1 | 5/2007 | Schlapfer et al. | |
| 2007/0129729 A1 | 6/2007 | Petit et al. | |
| 2007/0149909 A1 | 6/2007 | Fortin et al. | |
| 2007/0191846 A1 | 8/2007 | Bruneau et al. | |
| 2007/0198088 A1 | 8/2007 | Biedermann et al. | |
| 2007/0270820 A1 * | 11/2007 | Dickinson et al. | 606/61 |
| 2007/0270838 A1 * | 11/2007 | Bruneau et al. | 606/61 |
| 2008/0195149 A1 | 8/2008 | Burke | |

FOREIGN PATENT DOCUMENTS

| | | |
|---|---|---|
| DE | 4239716 | 8/1994 |
| EP | 0677277 | 3/1995 |
| EP | 0669109 | 8/1995 |
| FR | 2702363 | 3/1993 |
| FR | 2717370 | 9/1995 |
| FR | 2718946 | 10/1995 |
| FR | 2799949 | 4/2001 |
| GB | 2382304 | 5/2003 |
| JP | 2002224131 | 8/2002 |
| WO | WO 2005/039454 | 5/2005 |
| WO | WO 2005/044117 | 5/2005 |
| WO | WO 2005/092222 | 10/2005 |
| WO | WO 2005/094704 | 10/2005 |
| WO | WO 2005/110257 | 11/2005 |

OTHER PUBLICATIONS

Schwarzenbach O, Berlemann U, Stoll TM, Dubois G; Posterior Dynamic Stabilization Systems: DYNESYS; Orthop Clin North Am. Jul. 2005; 36(3):363-72.

Stoll TM, Dubois G, Schwarzenbach O: The Dynamic Neutralization System for the Spine: A Multi-center Study of a Novel Non-Fusion System; Eur Spine J. Oct. 2002; 11 Suppl 2:S170-8. Epub Sep. 10, 2002.

PCT Written Opinion of the International Search Report for PCT/US2007/072366.

* cited by examiner

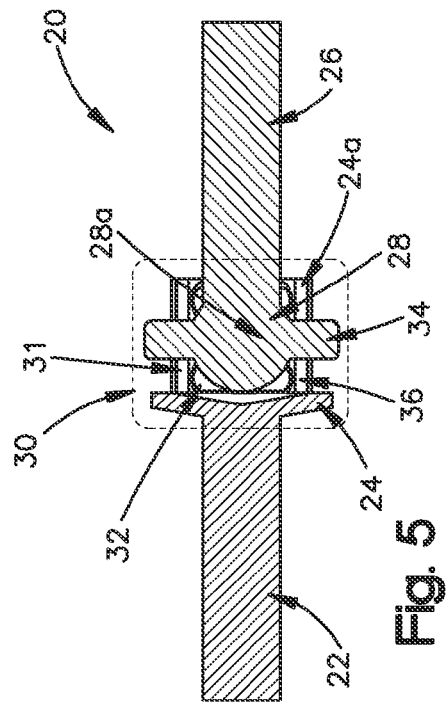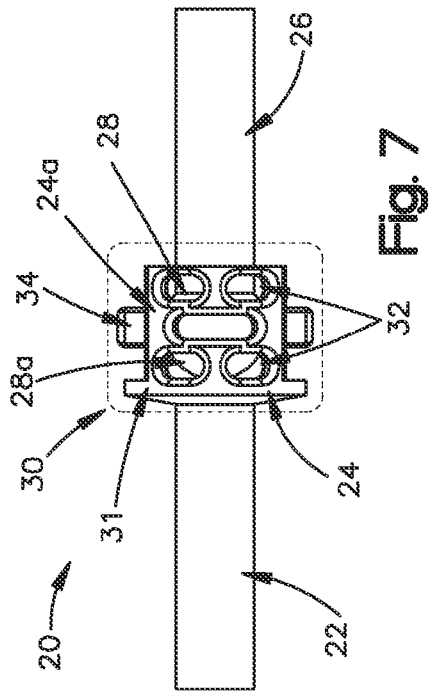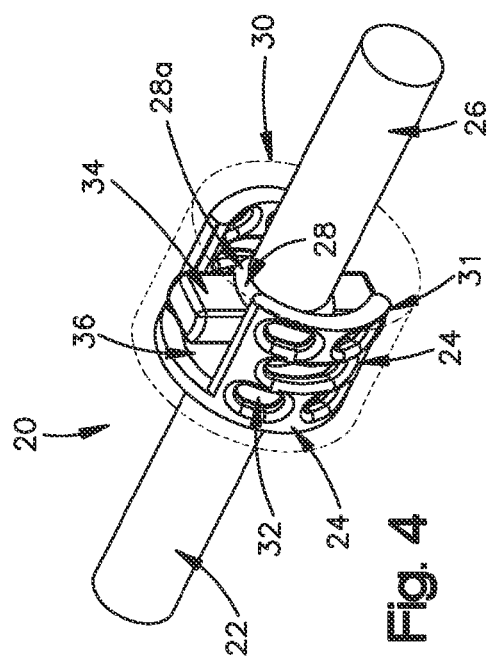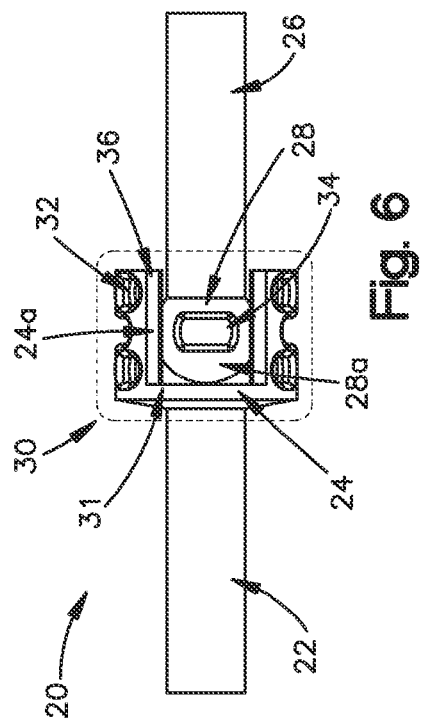

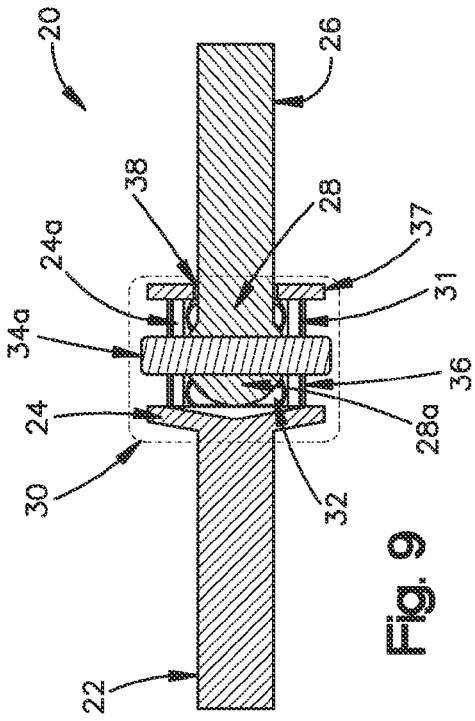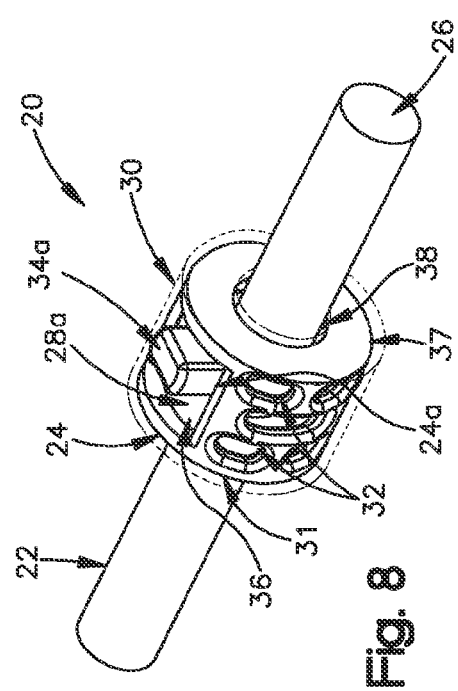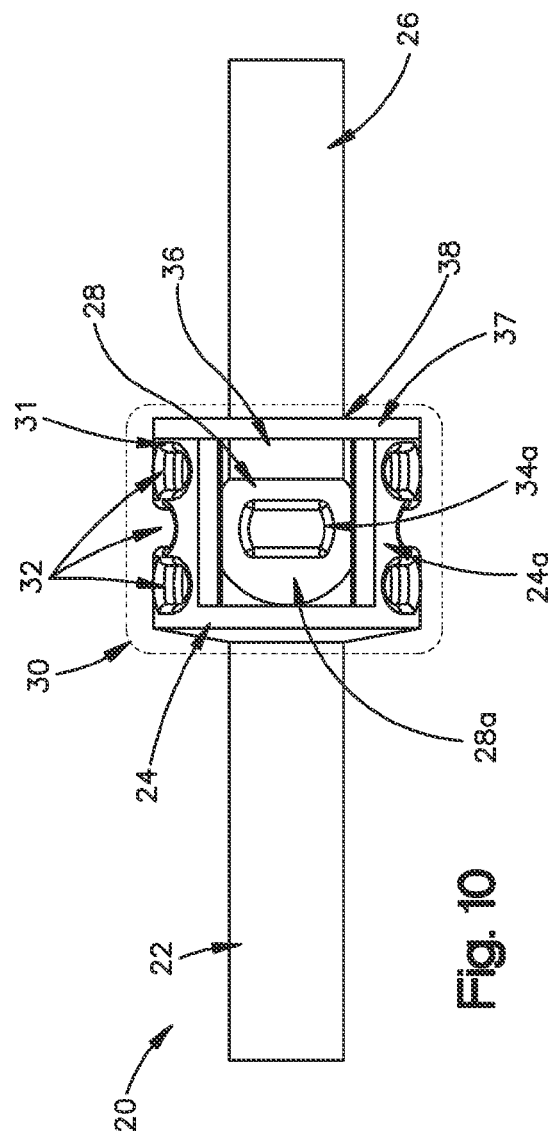

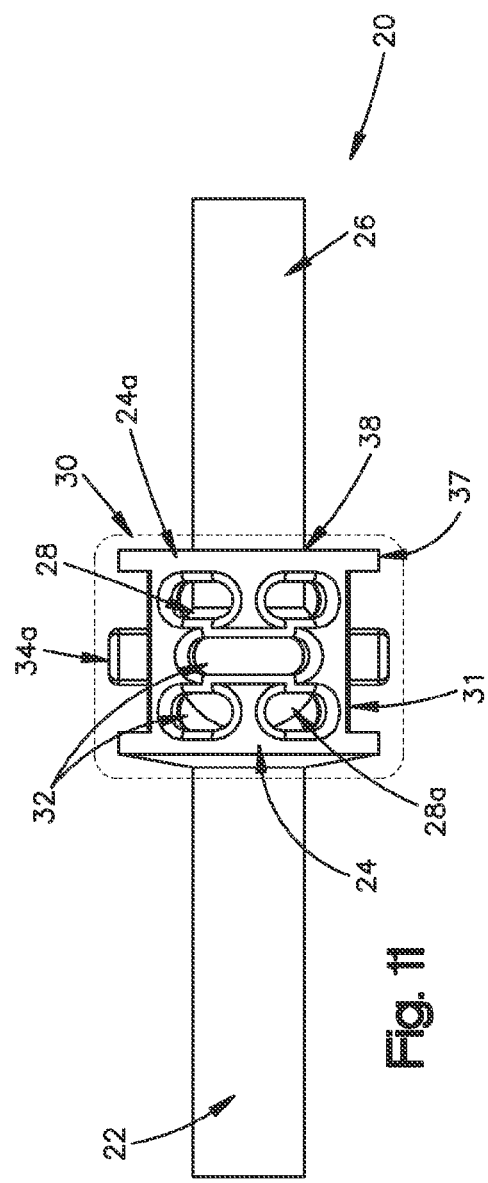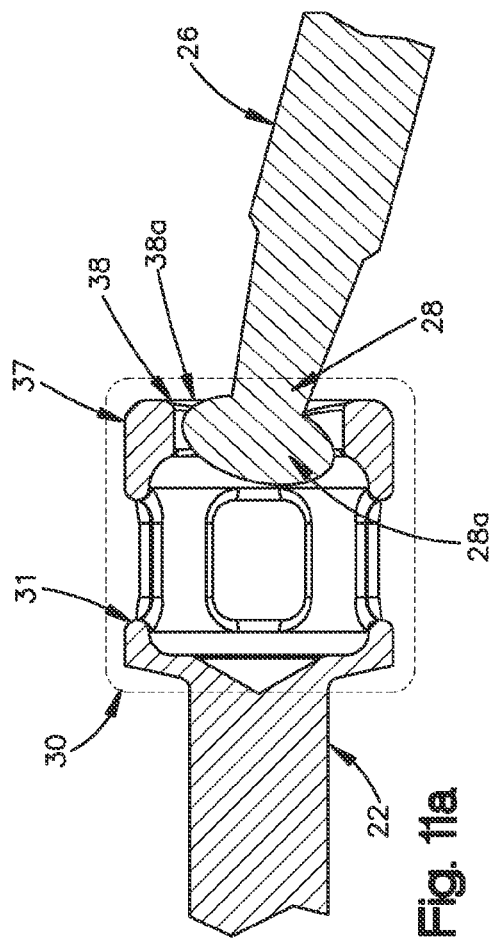

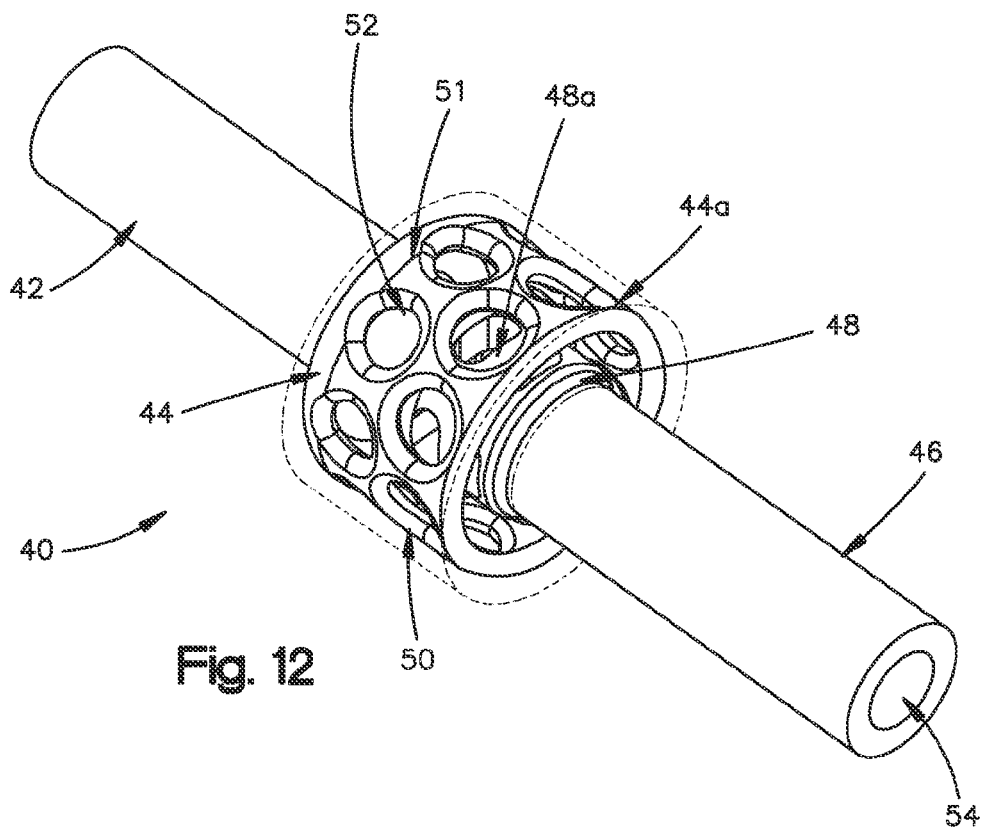
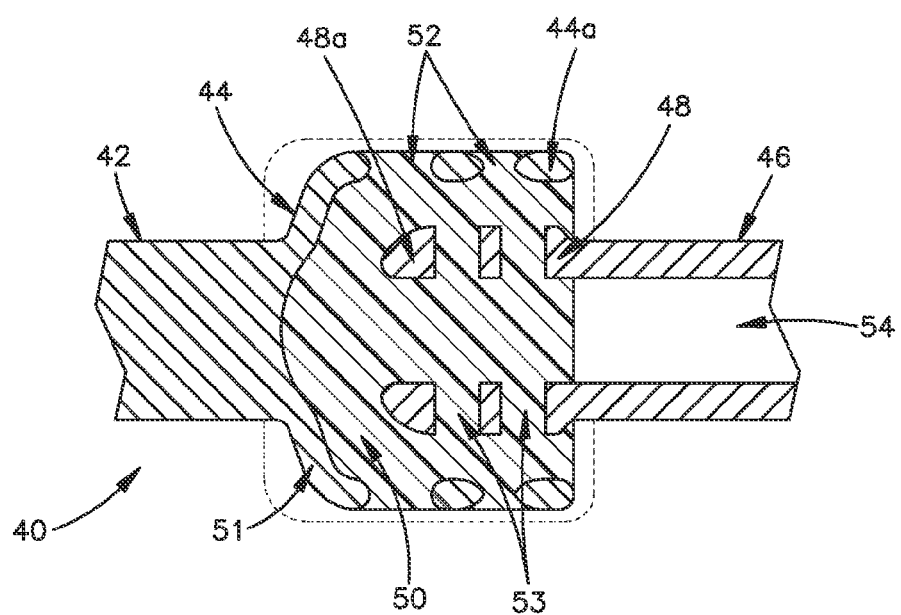

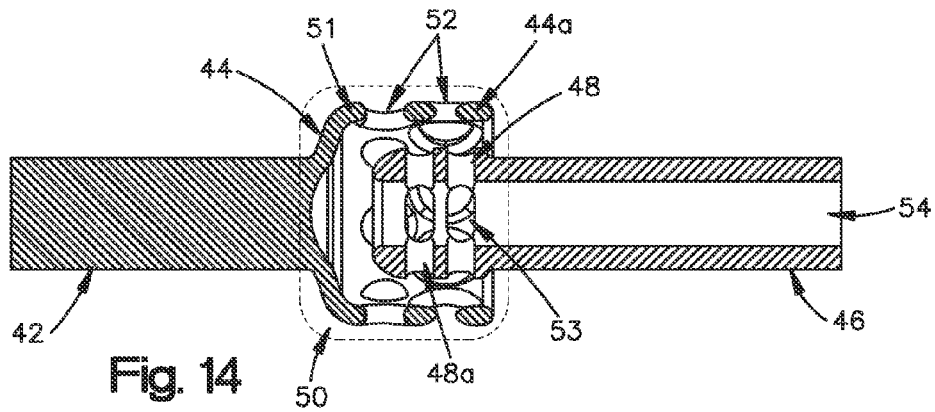
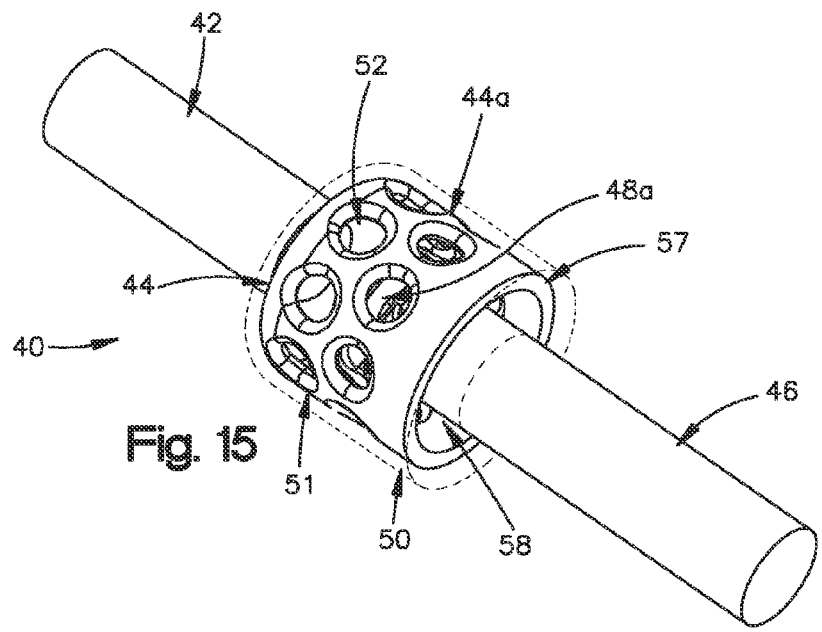
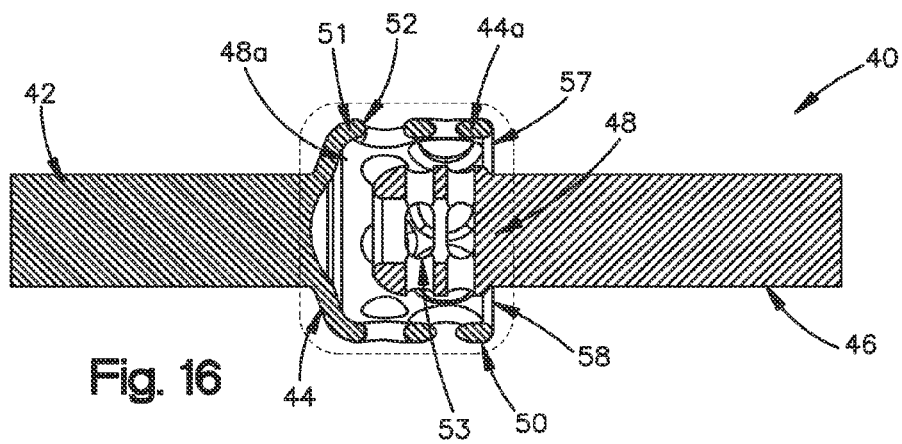

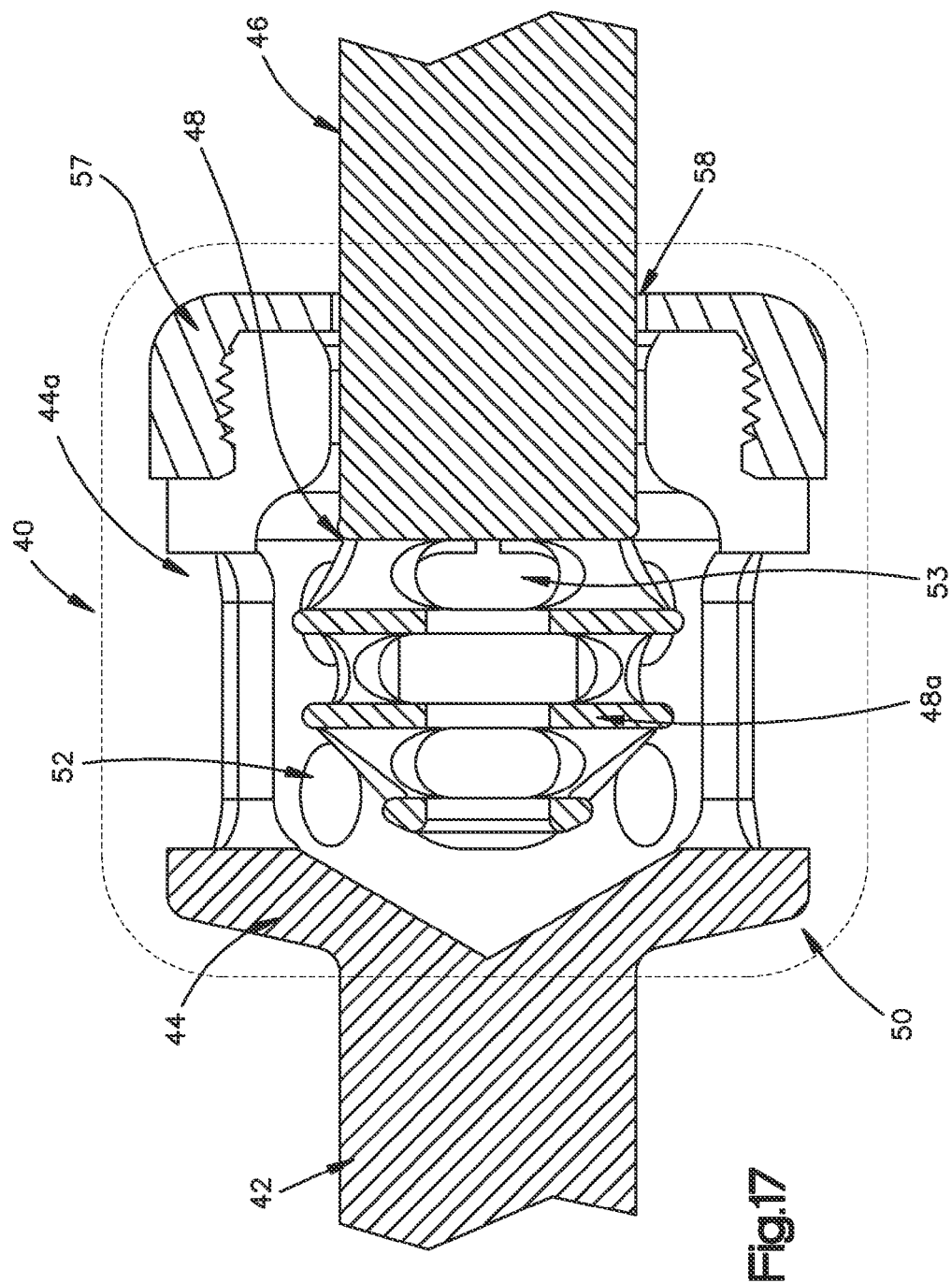

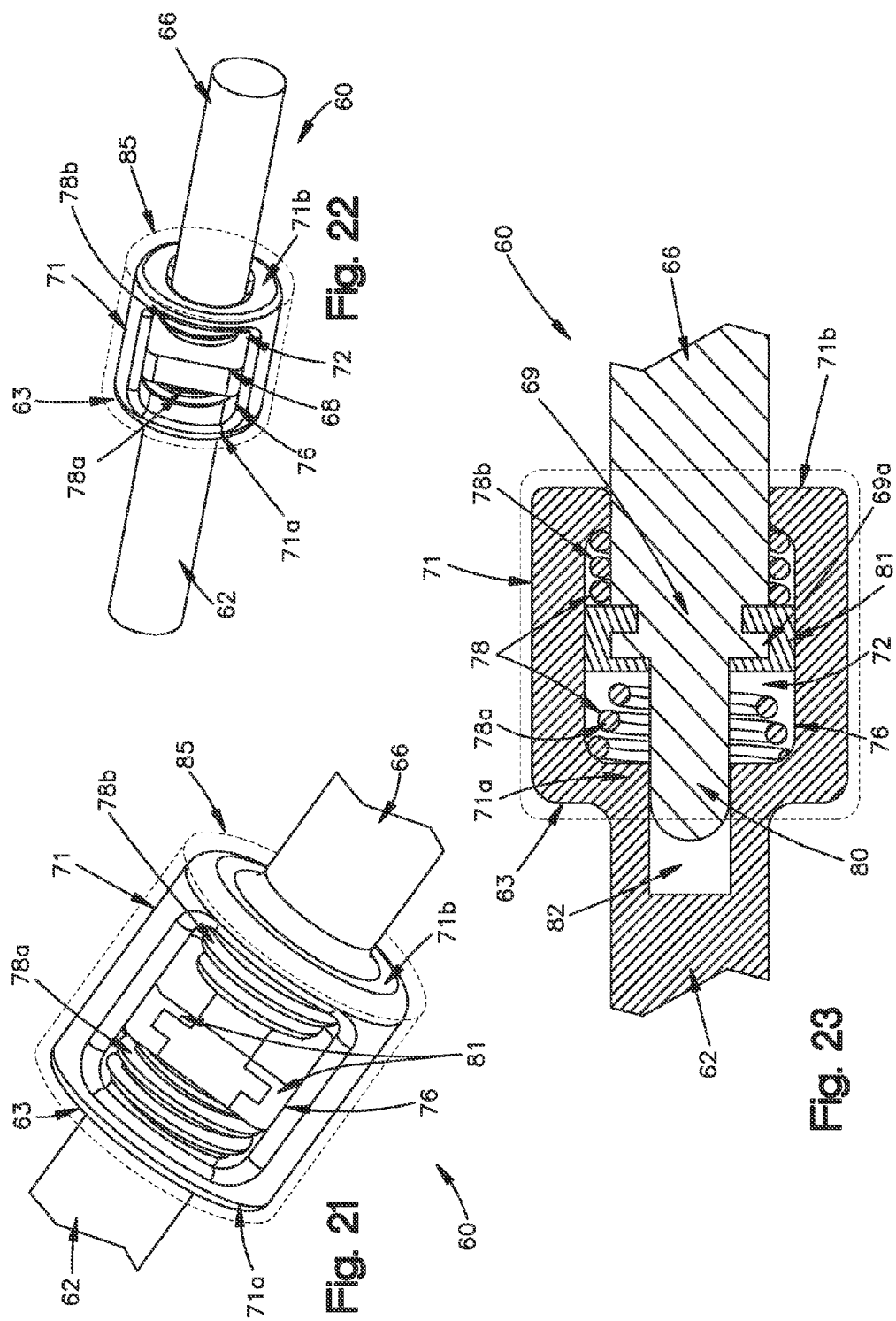

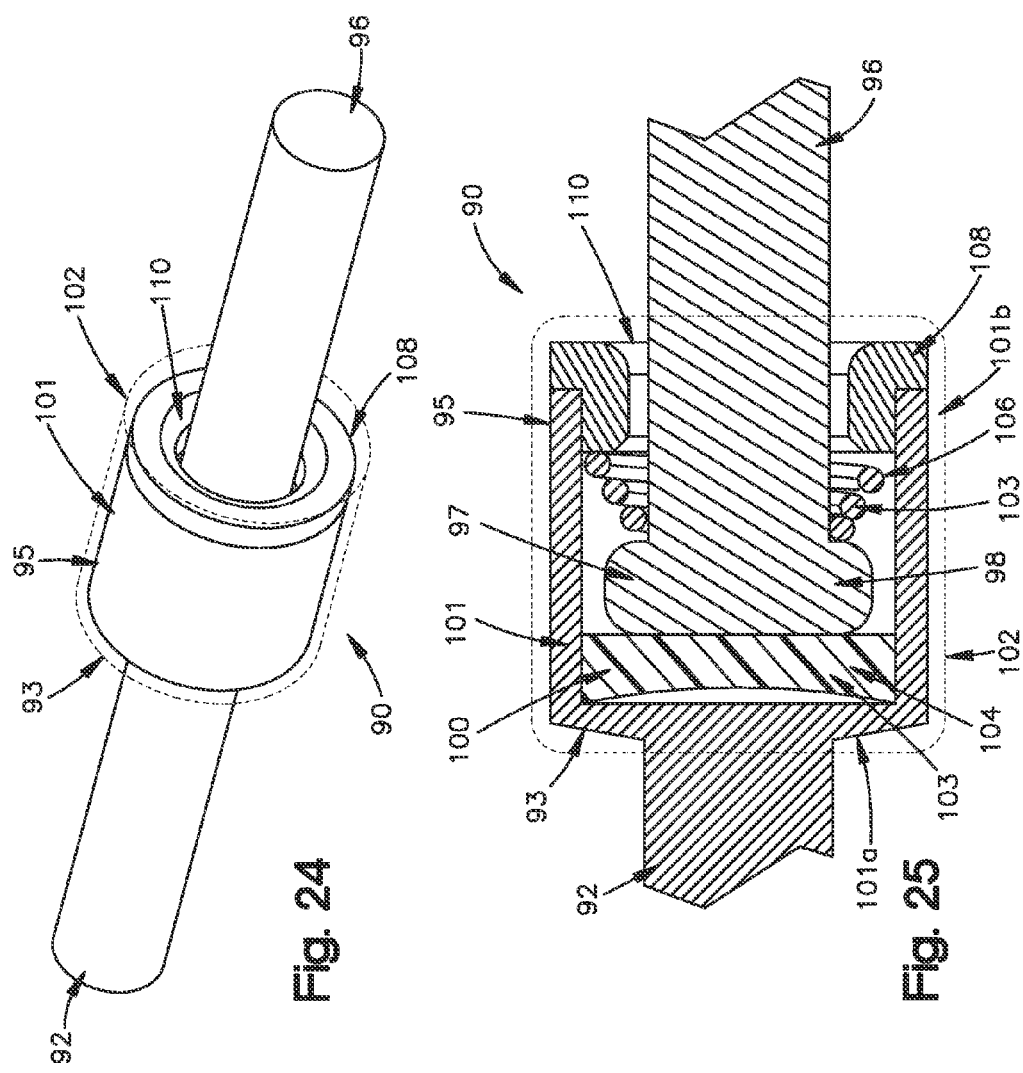

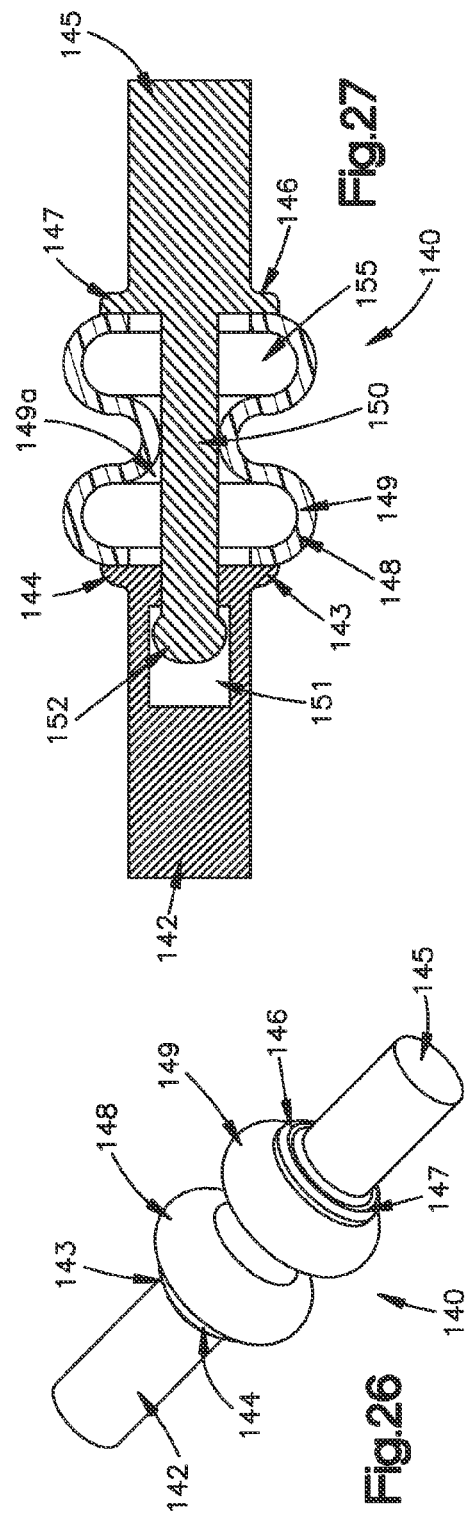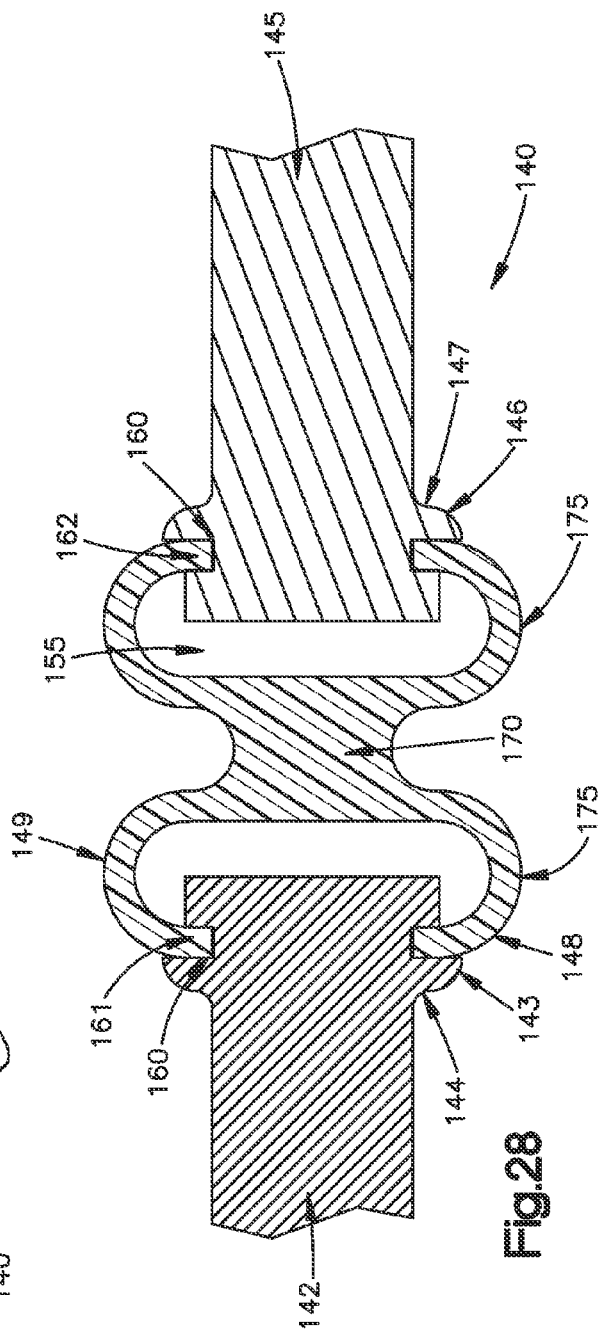

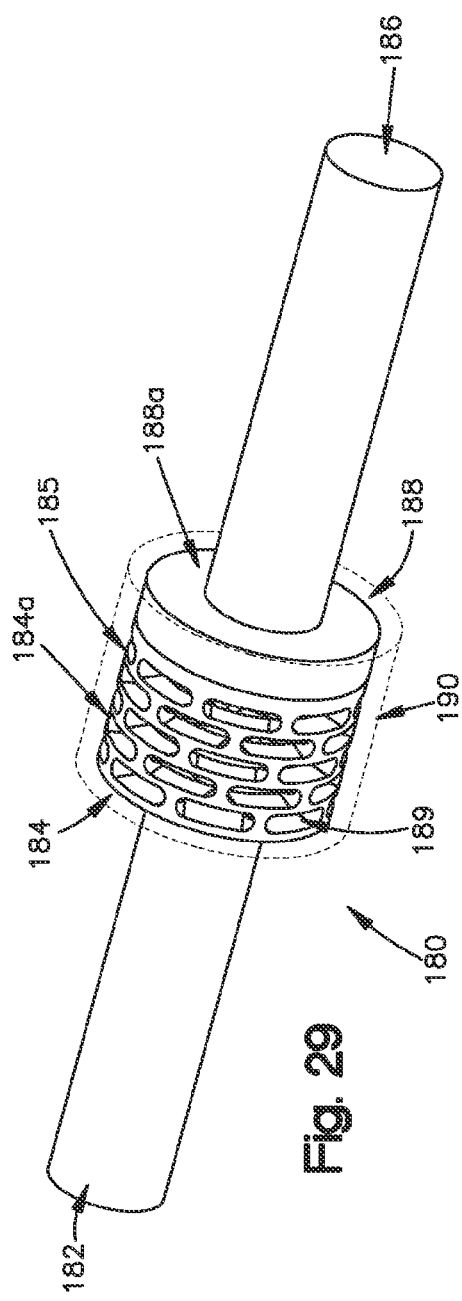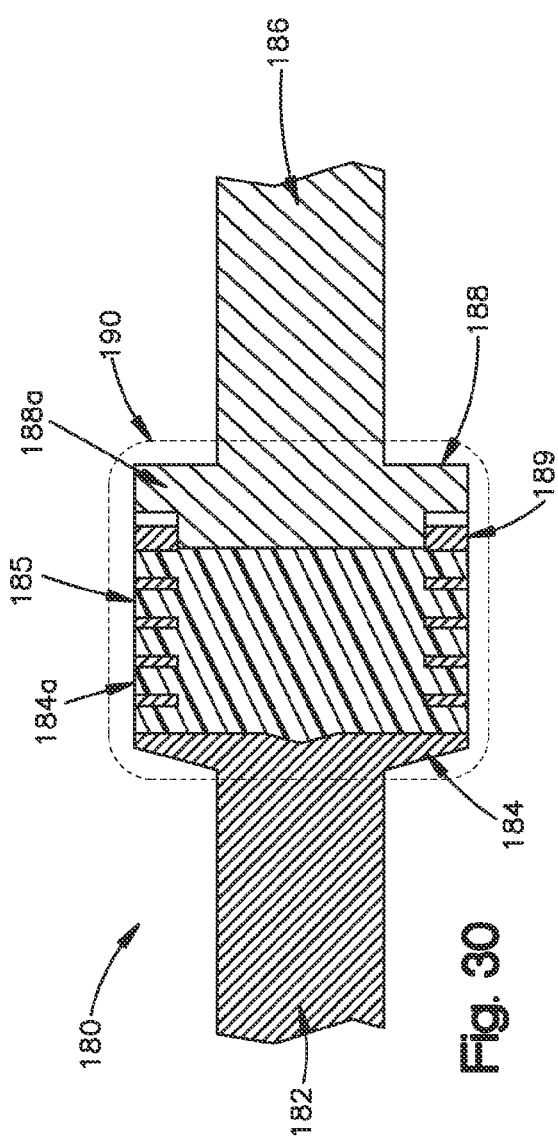

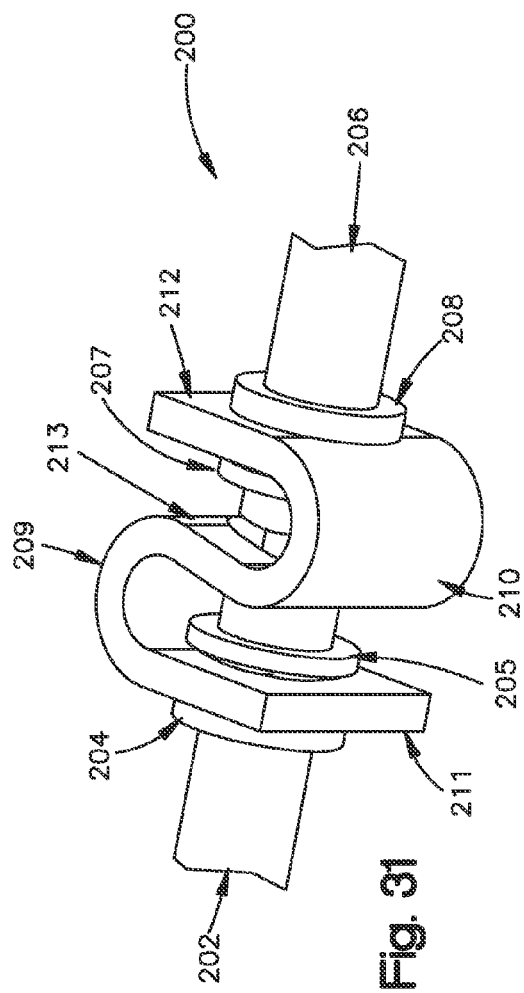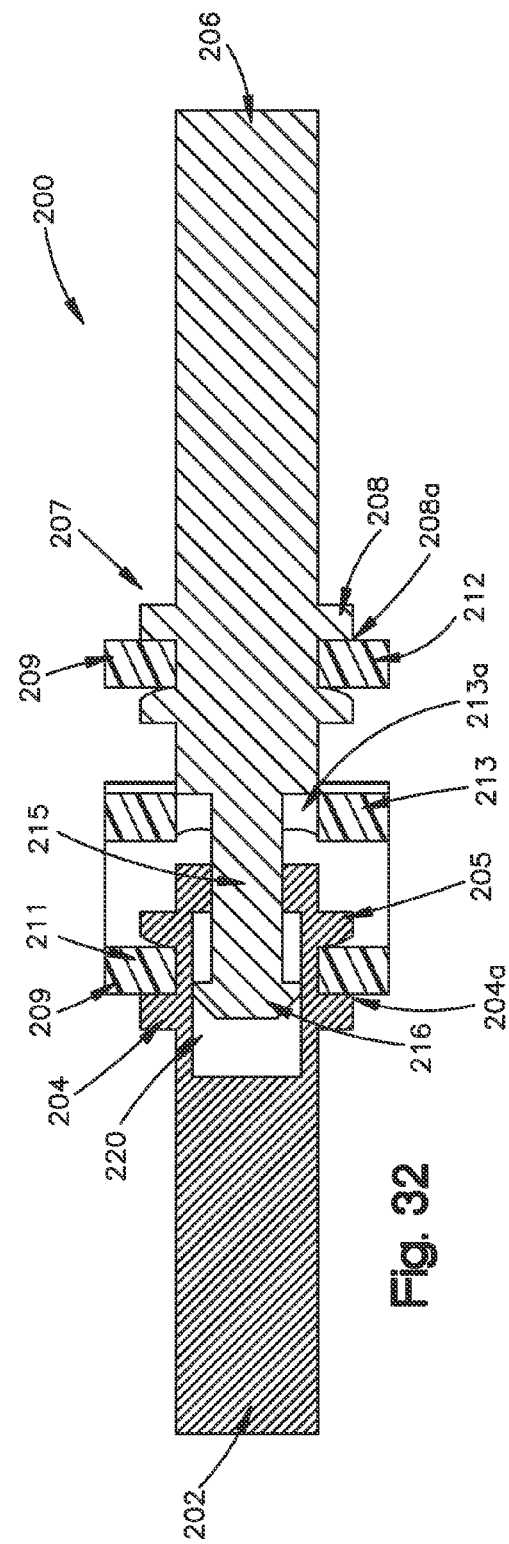

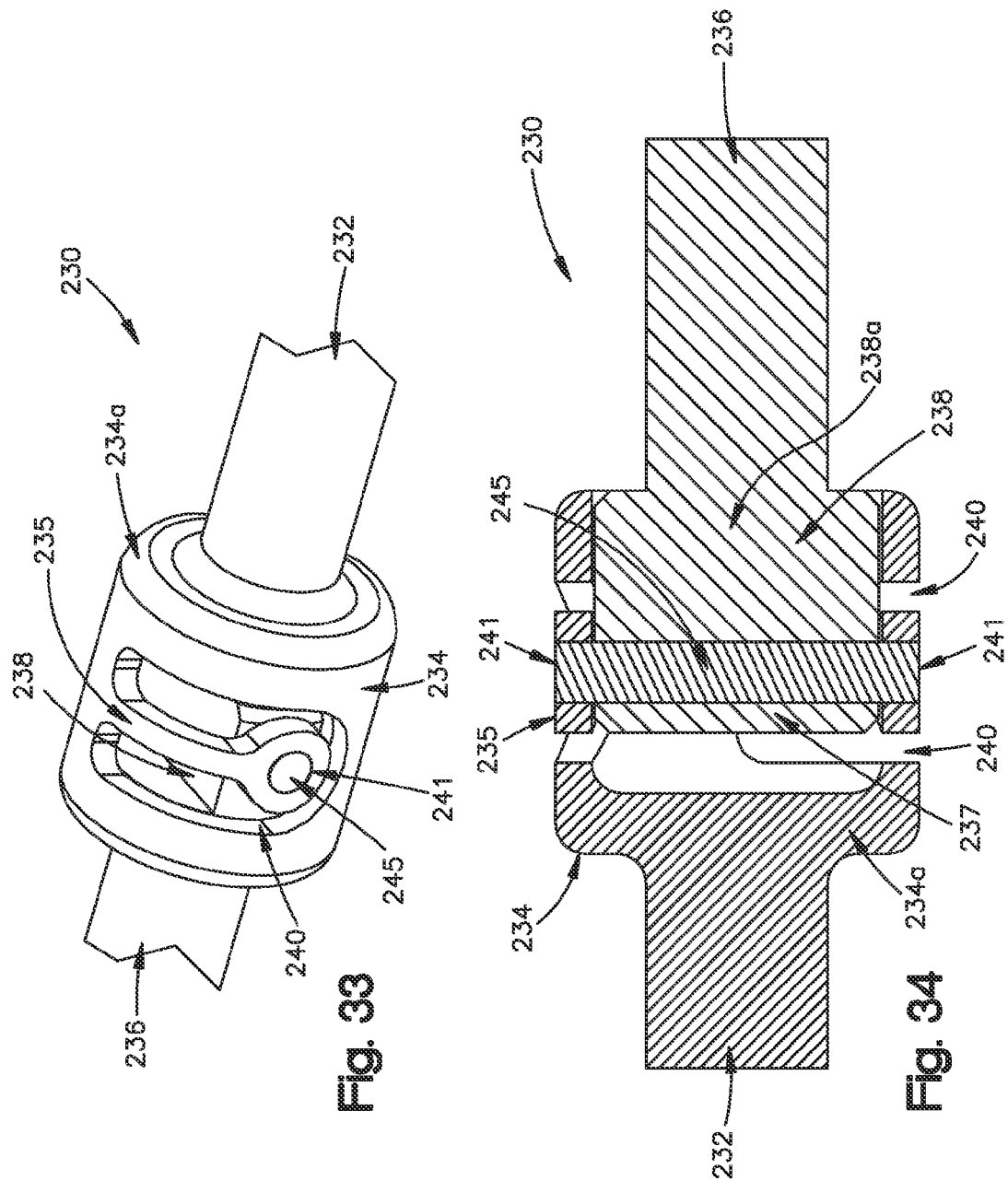

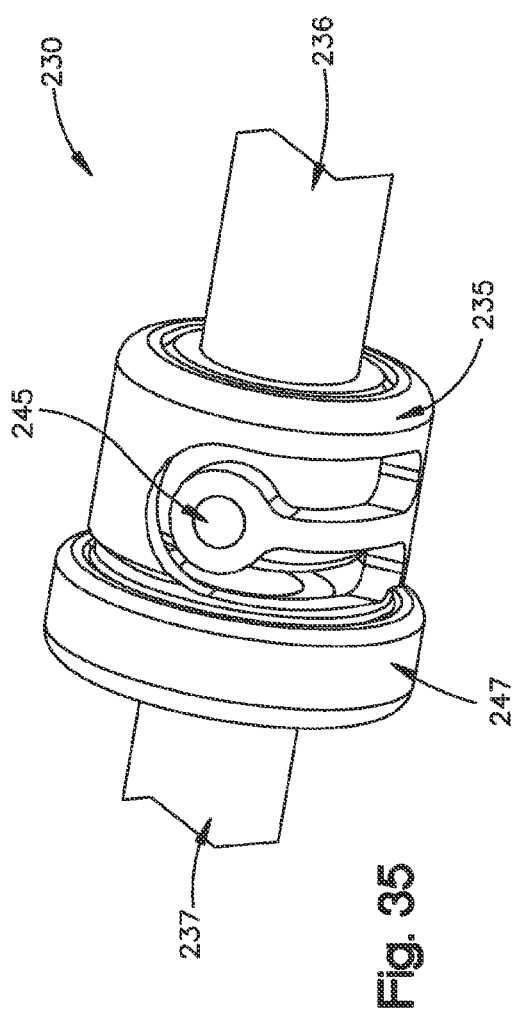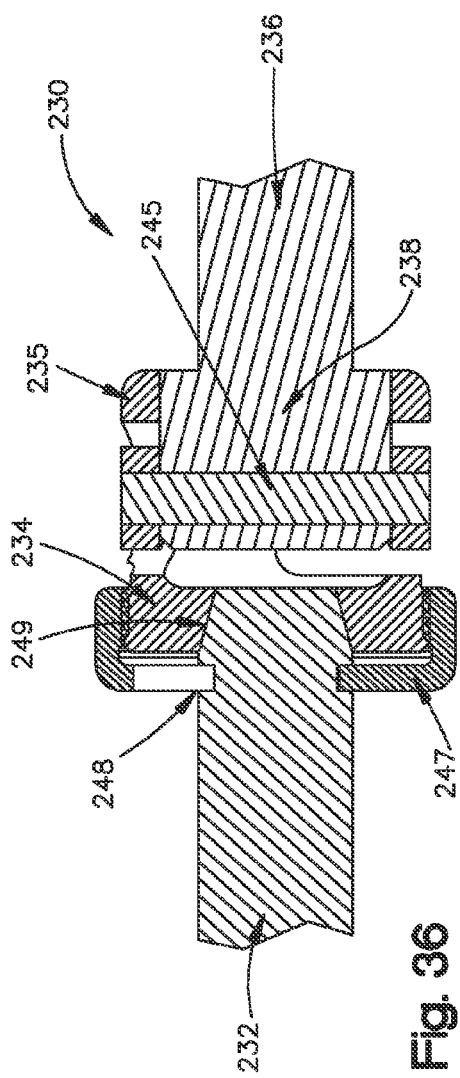

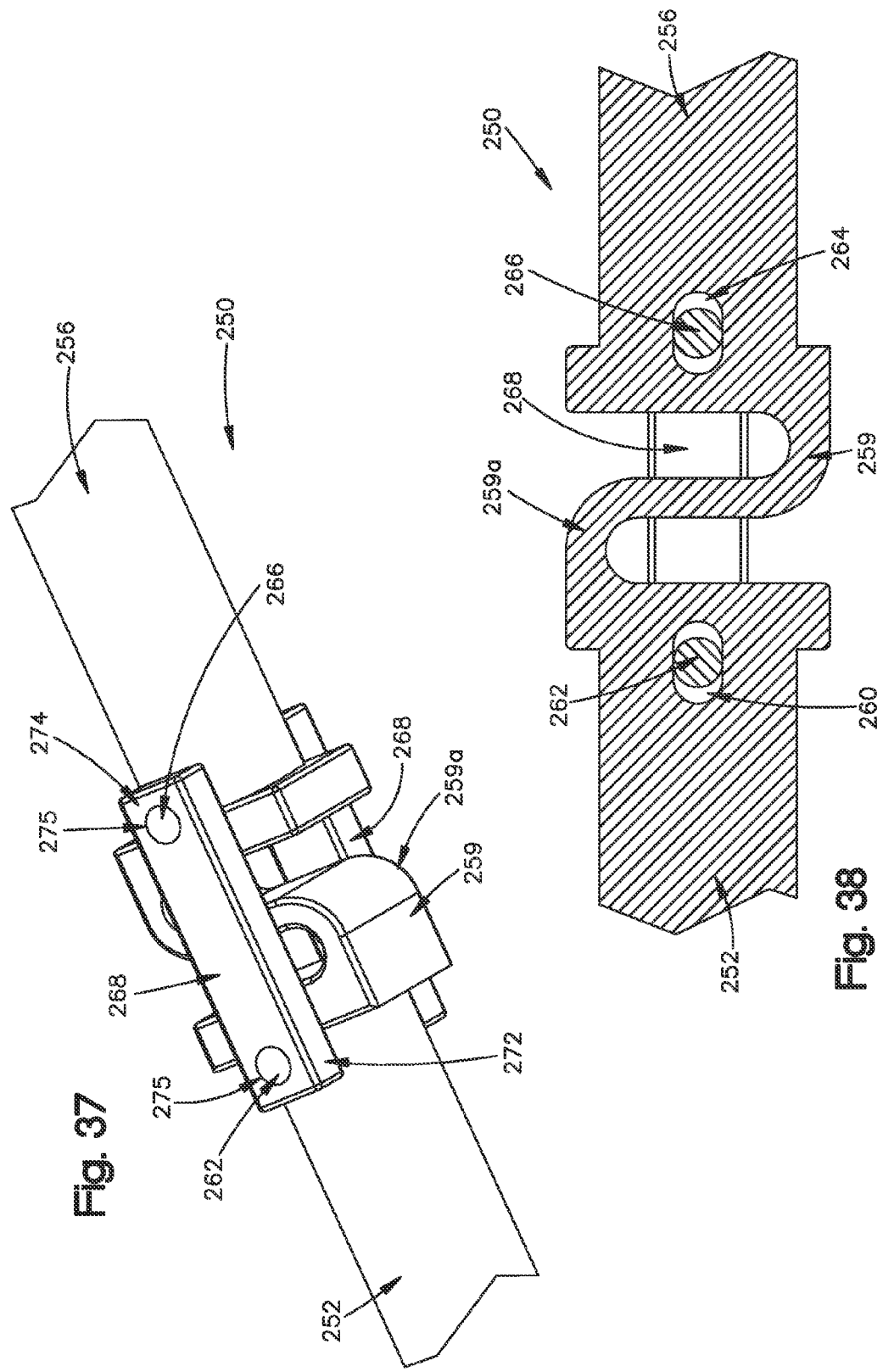

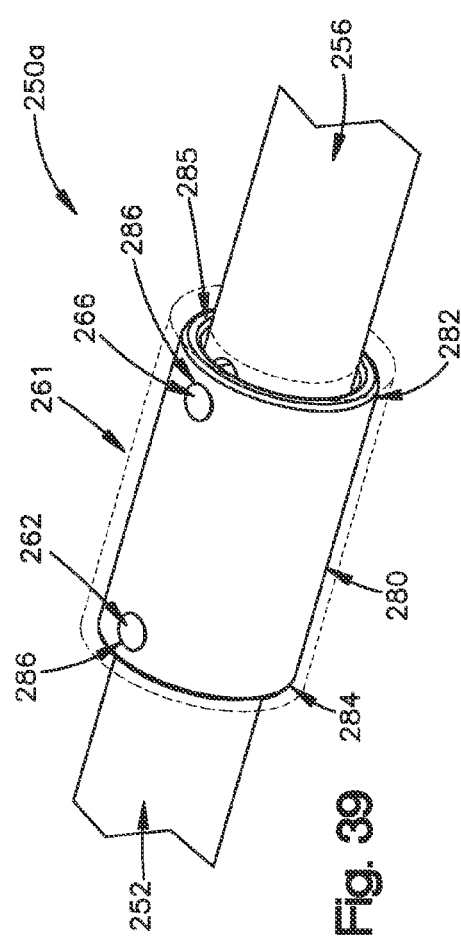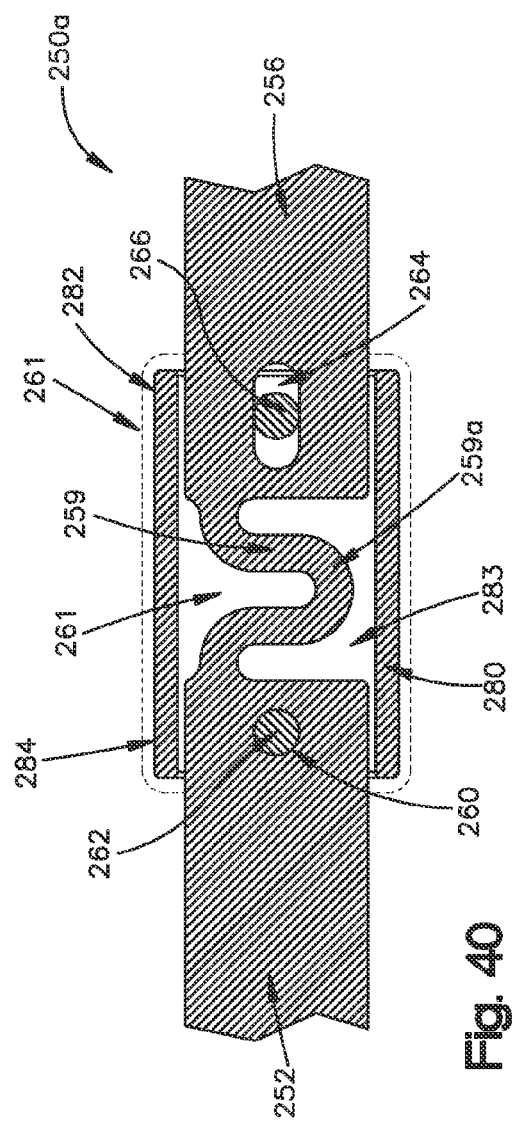

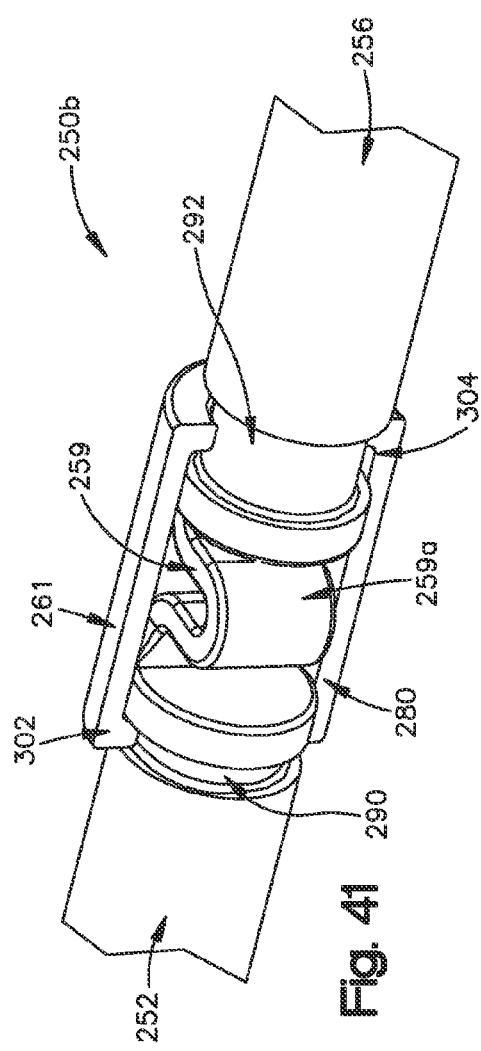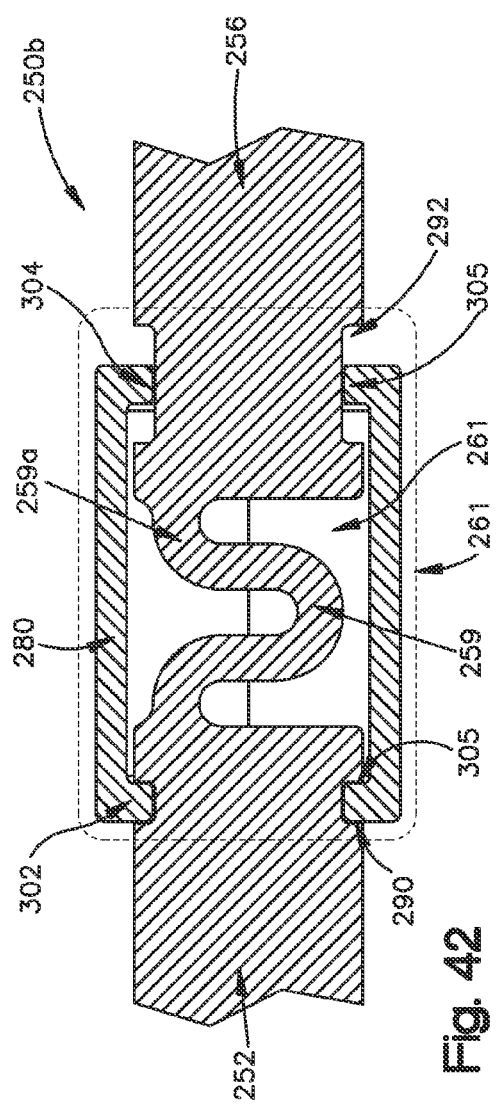

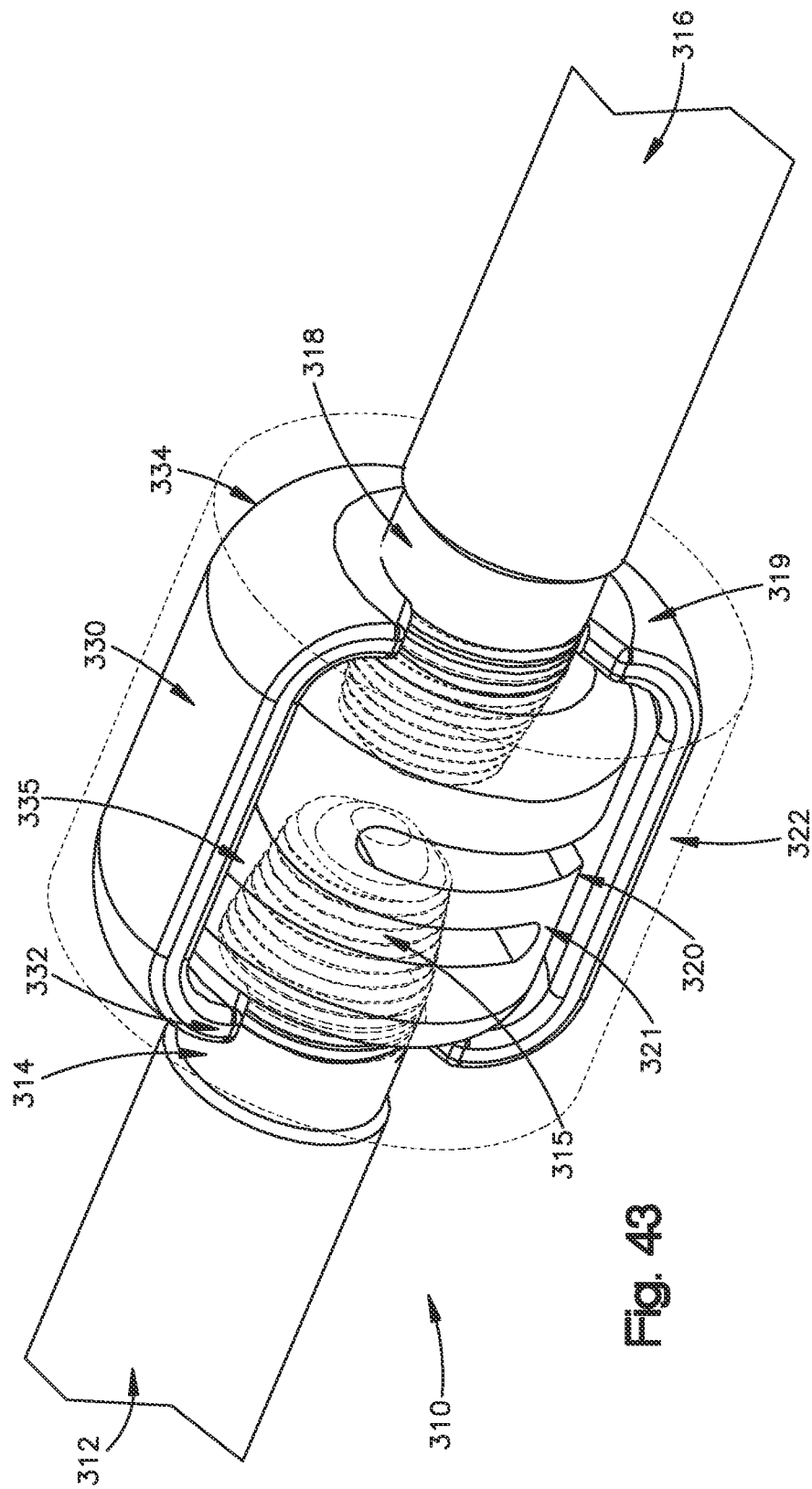

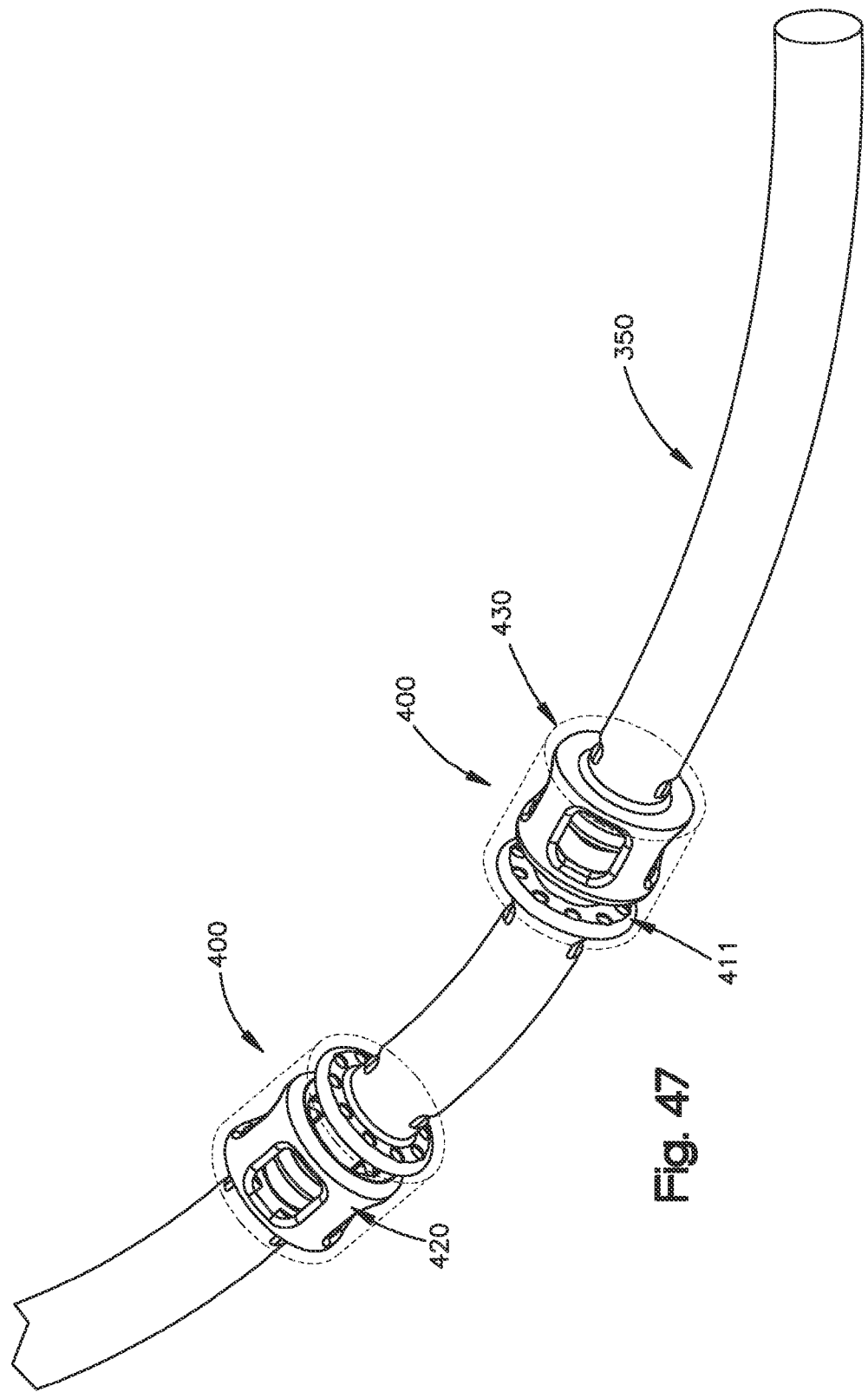

DYNAMIC FIXATION SYSTEM

CROSS-REFERENCE TO RELATED APPLICATIONS

This application claims the benefit of International Application No. PCT/US2007/072366, filed on Jun. 28, 2007, entitled "DYNAMIC FIXATION SYSTEM". This application also claims the benefit of priority of U.S. Provisional Application No. 60/817,474, filed on Jun. 28, 2006. The entire disclosure of these applications is incorporated herein by reference.

FIELD OF THE INVENTION

The invention relates to a fixation system, more specifically a dynamic spinal fixation system.

BACKGROUND OF THE INVENTION

Spinal fusion is a procedure that involves joining two or more adjacent vertebrae with a bone fixation device to restrict movement of the vertebra with respect to one another. For a number of known reasons, spinal fixation devices are used in spine surgery to align and/or fix a desired relationship between adjacent vertebral bodies. Such devices typically include a spinal fixation element, such as a relatively rigid fixation rod, that is coupled to adjacent vertebrae by attaching the fixation element to various bone fixation elements, such as hooks, bolts, wires, screws, etc. The fixation elements can have a predetermined contour, and once installed, the fixation element holds the vertebrae in a desired spatial relationship, either until desired healing or spinal fusion has taken place, or for some longer period of time.

Recently, there has been a movement away from the use of rigid fixation elements and more towards dynamic or flexible fixation elements. Dynamic fixation elements are desirable because they reduce the stress inherent in a rigid fixation system, and absorb shock, for example, in the extension and compression of the spine. In addition, the removal of bone structure, such as facet joints or laminae, result in instabilities of the motion segments of the spine. Consequently, a fixation system should stabilize the motion segment in anteroposterior translation as well as in axial rotation. Both motion patterns result in shear stress within the rods of the fixation system. This is especially important in elderly patients, where the bone quality is sometimes compromised, becoming sclerotic or osteoporotic.

Existing dynamic fixation systems incorporate mechanisms to absorb shock, for example, in extension and/or compression of the spine, but existing dynamic fixation systems generally lack sufficient strength and/or constraints to overcome expected shear stresses as a result of anteroposterior translation and/or axial rotation of the spine.

Thus, it is desirable to have a dynamic fixation system which can withstand the expected stresses including shear stresses caused by anteroposterior translation and/or axial rotation.

SUMMARY OF THE INVENTION

The dynamic fixation system may include one or more bone fixation elements for engaging one or more bones, preferably one or more vertebrae so that the dynamic fixation system spans two or more adjacent vertebrae for stabilization of the vertebrae. The dynamic fixation system may include a first rod having first and second ends and a second rod having first and second ends, wherein one of the ends of the first rod is operatively associated with one of the ends of the second rod so that the attached bones (e.g. vertebrae) are permitted to move with respect to one another. The dynamic fixation system may also include a damping component for joining the first and second ends of the first and second rods and for preventing the first and second rods from separating. The damping component being selected from one of a gel core, a hydrogel, a silicon, an elastomeric material, a rubber or a combination thereof. Preferably, the damping component is a polycarbonate urethane. Alternatively and/or in addition, the dynamic fixation system may include a damping mechanism for joining the first and second ends of the first and second rods and for preventing the first and second rods from separating.

The dynamic fixation systems may be connected together to form modular construct so that in use, a plurality of dynamic fixation systems may be connected to a patient's vertebrae via a plurality of bone fixation elements to stabilize the vertebrae. As generally understood by one of ordinary skill in the art, two, three or more constructs may be joined together in order to span two, three or more vertebrae. In use, the plurality of dynamic fixation systems are sized and configured to interact with one another to permit relative movement (e.g., translational, articulation, rotational (e.g. twisting), etc.) while being sized and configured to absorb and transmit the necessary loads. Alternatively and/or additionally, one or more of the dynamic fixation systems may be connected to a substantially rigid rod. In this manner, combinations of rigid fusion and dynamic fixation can be tailored for individual patients.

In situ, as a patient's vertebrae move, the movement (e.g., translation, articulation, rotation (e.g. twisting), etc.) and associated loads are transferred from the attached vertebrae to the rods via the bone fixation elements, and from the rods to the damping component and/or damping mechanism and back to the rods.

In one embodiment, the dynamic fixation system may include a first rod having first and second ends, a second rod having first and second ends, and a damping component located between one of the ends of the first rod and one of the ends of the second rod. Preferably, one of the ends of one of the first and second rods is in the form of a housing having an inner cavity for slidably receiving one of the ends of the other rods, more preferably for receiving at least one diametrically enlarged end portion formed on the other of the rod. More preferably, the other rod includes at least two diametrically enlarged end portions. The inner cavity of the housing being sized and configured to receive, at least, the outermost diametrically enlarged end portion. That is, the outermost diametrically enlarged end portion is preferably sized and configured to be received within the inner cavity of the housing. The inner diametrically enlarged end portion may be sized and configured with a diameter that is larger than, smaller than or equal to the diameter of the inner cavity. If the inner diametrically enlarged end portion has a diameter greater than or equal to the diameter of the inner cavity than the inner diametrically enlarged end portion can not be slidably received within the inner cavity of the housing and instead may act as a stop or stopping mechanism, and thus constrain, limit and/or control the amount of movement between the first and second rods. Alternatively, if the inner diametrically enlarged end portion is sized and configured with a diameter that is smaller than the diameter of the inner cavity of the housing than the inner diametrically enlarged end portion may be slidably received within the inner cavity of the housing and may constrain, limit and/or control the amount of movement between the first and second rods in this manner. The outermost diametrically enlarged end portion is preferably formed substantially adjacent to the end of the rod while the inner diametrically enlarged end portion is preferably formed somewhere in between the outermost diametrically enlarged end portion and the other end of the first rod.

The dynamic fixation system may also include a damping component located between one of the ends of the first rod and one of the ends of the second rods, preferably between the housing and at least one of the diametrically enlarged end portions. The housing may include a plurality of holes dispersed around the periphery of the housing to allow the damping component to be injected into the housing. Alternatively and/or in addition, the innermost diametrically enlarged end portion may include a plurality of openings so that the damping component can be injected through the openings formed in the end portion. Alternatively and/or in addition, the damping component may be injected over and/or around the housing and at least one of the diametrically enlarged end portions.

In another embodiment, the dynamic fixation system may include a first rod having a first end and a second end, a second rod having a first end and a second end, and a damping component positioned between one of the ends of the first rod and one of the ends of the second rod. The end portions of the first and second rods may be diametrically enlarged end portions. The dynamic fixation system may also include a housing, the housing being sized and configured to span and/or join one of the ends of the first rods with one of the ends of the second rods. The housing further being sized and configured to encapsulate and/or surround the damping component. The diametrically enlarged end portions of the first and second rods preferably include a plurality of holes so that the housing can be interwoven into the holes. Alternatively and/or in addition, the damping component may be injected into the housing and between the end portions of the first and second rods via the holes.

In another embodiment, the dynamic fixation system may include a first rod having first and second ends, a second rod having first and second ends and a damping component positioned between one of the ends of the first rod and one of the ends of the second rod. Preferably one of the ends of the first and second rods includes a diametrically enlarged end portion, more preferably an arcuate end portion, while one of the ends of the other rod includes a housing having an inner cavity for receiving the preferred arcuate end portion so that the arcuate end portion can move with respect to the housing, and hence the rods can move with respect to each other. The damping component may be located between the housing and the preferred arcuate end portion. Preferably, the housing may include a plurality of holes to permit the damping component to be injected into the housing. The damping component may also be injected molded over and/or around the housing and preferred arcuate end portion. Alternatively and/or in addition, the housing may also include one or more slots, the slots being sized and configured to receive one or more tabs formed on the preferred arcuate end portion to constrain, limit and/or control the amount of movement between the first and second rods with respect to each other. The housing may also include an optional end cap to provide additional protection to prevent the first and second rods from becoming separated with respect to one another.

In another embodiment, the dynamic fixation system may include a first rod having first and second ends, a second rod having first and second ends, a damping component located between one of the ends of the first rod and one of the ends of the second rod. Preferably, one of the ends of the first and second rods is in the form of a housing. The housing having an inner cavity and a window formed on a side thereof. The inner cavity being sized and configured to receive one of the ends of the other rod which is preferably sized and configured to be operatively associated with a plate like member so that, after the end of the rod has been inserted into the inner cavity of the housing, the plate like member may be connected to the end of the rod through the window so that the plate like member may engage the end of the rod to secure the first and second rods with respect to one another. The damping component may be injected molded into the inner cavity via the window. The damping component may be injected above, below and/or around the plate like member so that the damping component substantially fills the inner cavity, including the window. Additionally and/or alternatively, the damping component may be injection molded over and/or around the housing.

In another embodiment, the damping component may be replaced by a damping mechanism, such as, for example, one or more springs. Preferably the damping mechanism may be located within the inner cavity of the housing. More preferably, the dynamic fixation system includes at least two springs, one on either side of the plate like member and the housing. The dynamic fixation system may also include a guiding feature to assist in axially guiding the first and second rods with respect to one another. The axially guiding feature may be in the form of a projection extending from one of the rods, the projection being sized and configured to engage a recess formed in the other of the rods. Additionally, the dynamic fixation system may also include a damping component in combination with the damping mechanism.

In another embodiment, the dynamic fixation system may include a first rod having first and second ends, a second rod having first and second ends, and a damping mechanism located between one of the ends of the first rod and one of the ends of the second rods. Preferably one of the ends of the first and second rods is in the form of a housing, the housing having an inner cavity sized and configured to receive one of the ends of the other rod, which preferably is in the shape of a diametrically enlarged end portion. Preferably, the housing is sized and configured to receive the diametrically enlarged end portion to so that the first and second rods may move with respect to each other. The damping mechanism may include a plurality of spring like members located between the housing and the diametrically enlarged end portion. Additionally, the dynamic fixation system may also include an optional damping component in combination with the damping mechanism, the damping component may be injection molded into the inner cavity of the housing and/or molded over and/or around the housing. The dynamic fixation system may also include a locking cap to provide additional protection to prevent the first and second rods from separating from one another.

In another embodiment, the dynamic fixation system may include a first rod having first and second ends, a second rod having first and second ends, and a damping mechanism joining one of the ends of the first rod to one of the ends of the second rod. The ends of the first and second rods may be in the form of diametrically enlarged ends. The damping mechanism may be in the form of a damper, preferably a collapsible damper, so that the first and second rods may move with respect to each other. That is, in use, the damper may act like a spring element facilitating movement between the first and second rods. In addition, one of the rods may include a recess formed therein for slidably receiving a projection formed in the other of the rods for constraining and/or limiting movement between the first and second rods. Alternatively and/or in addition, the damper may be partially or completely filled with a damping component.

In another embodiment, the dynamic fixation system may include a first rod having first and second ends and a second rod having first and second ends wherein one of the ends of the first rod contacts one of the ends of the second rod. Preferably, one of the ends of the first rod includes a diametrically enlarged end portion while one of the ends of the other rod is in the form of a housing. The housing preferably incorporating a plurality of slots and/or holes so that the housing is flexible. In this manner, the housing can act as a spring-like member facilitating movement between the first and second rods. Alternatively and/or additionally, the housing may be partially or completely filled with a damping component. The damping component may be injected molded into the housing, preferably via the plurality of slots and/or holes. The damping component may also be injection molded over and/or around the housing.

In another embodiment, the dynamic fixation system may include a first rod having first and second ends, a second rod having first and second ends and a damping mechanism joining one of the ends of the first rod with one of the ends of the second rod. The damping mechanism preferably is in the form of a spring, more preferably an S-shaped spring having a first end and a second end wherein the first end of the spring is operatively associated with one of the rods and the second end is operatively associated with the other rod so that the first and second rods may move with respect to each other. Alternatively and/or in addition, one of the rods may include a recess formed therein for slidably receiving a projection extending from the other rod The dynamic fixation system may also include constraining means for constraining, limiting and/or controlling the amount of movement between the first and second rods. The constraining means may be in the form of one or more bars that may be operatively connected to the first and second rods. The bars may include first and second ends, each of the ends including at least one hole for receiving a locking bolt to secure the bars to the ends of the first and second rods. Preferably, at least one of the holes formed in the bars and/or rods is in the form of an elongated hole so that axial movement between the bars and the rods is permitted.

Alternatively, the constraining means may be in the form of a sleeve that may be operatively connected to the first and second rods. The sleeve may include first and second ends and a central through bore, the central through bore may be sized and configured to receive at least a portion of the first and second rods and the damping mechanism. Each of the first and second ends preferably include at least one hole for receiving a locking bolt to secure the sleeve to the ends of the first and second rods. Preferably, at least one of the holes formed in the sleeve and/or rods is in the form of an elongated hole so that axial movement between the sleeves and the rods is permitted. Alternatively, the sleeve may include one or more projections extending inwardly from the first and second ends thereof, the projections being sized and configured to engage circumferential notches formed in the ends of the rods. Preferably, one or both of the notches may be sized and configured to be wider than the projection received therein so that the first and second rods may move with respect to each other. The dynamic fixation system may also include a damping component disposed in the space between the sleeve and the damping mechanism. Additionally and/or alternatively, the damping component may be injection molded around and/or over the sleeve.

In another embodiment, the dynamic fixation system may include a first rod having first and second ends and a second rod having first and second ends wherein one of the ends of the first rod is preferably operatively associated with one of the ends of the second rod. More preferably, one of the ends of the rods is sized and configured to be slidably received within one of the ends of the other rod. One of the ends of one of the rods may be in the form of a housing having an inner cavity for slidably receiving the end of the other rod, which is preferably in the form of an enlarged end portion. The housing may also include a plurality of slots and/or holes so that the housing may be flexible and act as a spring-like member to facilitate movement between the first and second rods. The dynamic fixation system may also incorporate a locking bolt to secure the ends of the rods with respect to each other. The dynamic fixation system may also include an end sleeve to constrain, limit and/or control the amount of movement between the first and second rods. In addition, the end sleeve may provide additional protection in preventing the first and second rods from separating with respect to each other. Preferably, the end sleeve interconnects one of the rods with the housing.

BRIEF DESCRIPTION OF THE DRAWINGS

The system is explained in even greater detail in the following exemplary drawings. The drawings are merely exemplary to illustrate the structure of preferred devices and certain features that may be used singularly or in combination with other features. The invention should not be limited to the embodiments shown.

FIG. 4 is a perspective view of an alternative embodiment of a dynamic fixation system;

FIG. 5 is a cross-sectional view of the dynamic fixation system of FIG. 4;

FIG. 6 is a side view of the dynamic fixation system of FIG. 4;

FIG. 7 is a side view of the dynamic fixation system of FIG. 4;

FIG. 8 is a perspective view of an alternative embodiment of a dynamic fixation system;

FIG. 9 is a cross-sectional view of the dynamic fixation system of FIG. 8;

FIG. 10 is a side view of the dynamic fixation system of FIG. 8;

FIG. 11 is a side view of the dynamic fixation system of FIG. 8;

FIG. 11a is a cross-sectional view of a dynamic fixation system incorporating an end cap and key-type arrangement;

FIG. 12 is a perspective view of an alternative embodiment of a dynamic fixation system;

FIG. 13 is a cross-sectional view of the dynamic fixation system of FIG. 12;

FIG. 14 is cross-sectional view of the dynamic fixation system of FIG. 12;

FIG. 15 is a perspective view of an alternative embodiment of a dynamic fixation system;

FIG. 16 is a cross-sectional view of the dynamic fixation system of FIG. 15;

FIG. 17 is an enlarged cross-sectional view of the dynamic fixation system of FIG. 15;

FIG. 21 is a perspective view of an alternative embodiment of a dynamic fixation system;

FIG. 22 is a perspective view of the dynamic fixation system of FIG. 21;

FIG. 23 is a cross-sectional view of the dynamic fixation system of FIG. 21;

FIG. 24 is a perspective view of an alternative embodiment of a dynamic fixation system;

FIG. 25 is a cross-sectional view of the dynamic fixation system of FIG. 24;

FIG. 26 is a perspective view of an alternative embodiment of a dynamic fixation system;

FIG. 27 is a cross-sectional view of the dynamic fixation system of FIG. 26;

FIG. 28 is an alternate cross-sectional view of the dynamic fixation system of FIG. 26;

FIG. 29 is a perspective view of an alternative embodiment of a dynamic fixation system;

FIG. 30 is a cross-sectional view of the dynamic fixation system of FIG. 29;

FIG. 31 is a perspective view of an alternative embodiment of a dynamic fixation system;

FIG. 32 is a cross-sectional view of the dynamic fixation system of FIG. 31;

FIG. 33 is a perspective view of an alternative embodiment of a dynamic fixation system;

FIG. 34 is a cross-sectional view of the dynamic fixation system of FIG. 33;

FIG. 35 is a perspective view of an alternative embodiment of a dynamic fixation system;

FIG. 36 is a cross-sectional view of the dynamic fixation system of FIG. 35;

FIG. 37 is a perspective view of an alternative embodiment of a dynamic fixation system;

FIG. 38 is a cross-sectional view of the dynamic fixation system of FIG. 37;

FIG. 39 is a perspective view of an alternative embodiment of a dynamic fixation system;

FIG. 40 is a cross-sectional view of the dynamic fixation system of FIG. 39;

FIG. 41 is a perspective view of an alternative embodiment of a dynamic fixation system;

FIG. 42 is a cross-sectional view of the dynamic fixation system of FIG. 41;

FIG. 43 is a cross-sectional view of an alternative embodiment of a dynamic fixation system;

FIG. 47 is a perspective view of a plurality of dynamic fixation systems joined to a substantially rigid fixation system.

DETAILED DESCRIPTION

Figure 1:
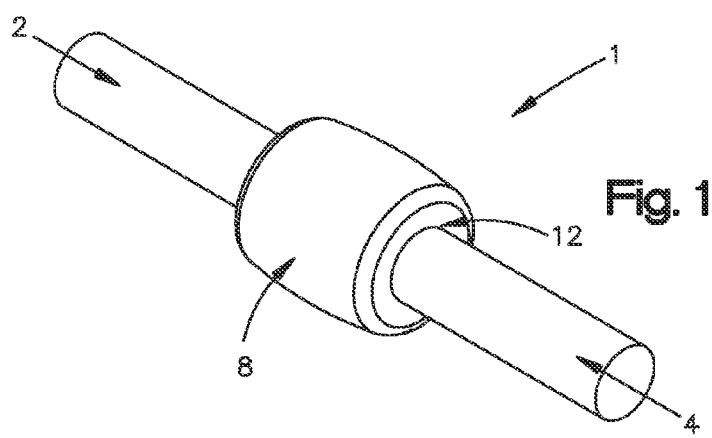
FIG. 1 is a perspective view of an exemplary embodiment of the dynamic fixation system.

Certain exemplary embodiments of the invention will now be described with reference to the drawings. In general, such embodiments relate to a fixation system, by way of non-limiting example, a dynamic fixation system for use in posterior spinal fixation. The invention may have other applications and uses and should not be limited to the structure or use described and illustrated. As will be described in greater detail below, the dynamic fixation system may include a first rod, a second rod, and a damping mechanism and/or damping component positioned between and/or connecting the first and second rods. The damping mechanism and/or damping component permits the first rod to move (e.g., translate, angulate, rotate (e.g. twist), etc.) with respect to the second rod.

The dynamic fixation system including but not limited to the first and second rods, the optional housing, cage, end portions, tabs, locking caps, spring elements, sleeves, damping mechanism, damper, etc., may be manufactured from any biocompatible material known in the art including, but not limited to, cobalt chromium, stainless steel, carbon fiber reinforced matrix, carbon fiber reinforced plastic, any other fibers known in the art, titanium, titanium alloys, plastics, etc.

The damping component may be made of, for example, a gel core, hydrogel, silicon, elastomeric components and/or materials, a rubber, or a combination thereof. Preferably, the damping component may be made of polycarbonate urethane (PCU). Preferably, the elasticity of the damping component may be higher than that of the remaining components of the dynamic fixation system including the first and second rods.

In situ, the dynamic fixation system may be sized and configured to engage one or more bone fixation elements, which engage one or more vertebrae so that the dynamic fixation system spans two or more adjacent vertebrae for stabilization (e.g., stabilizing or fixation) of the vertebrae with respect to one another. For example, the dynamic fixation system may be used in combination with an intervertebral implant. The dynamic fixation system may permit the vertebrae to settle (e.g. compress) over time, thus facilitating better fusion between the intervertebral implant and the adjacent vertebrae. Alternatively, the dynamic fixation system can be used in connection with an articulating intervertebral implant or any other implant known in the art, or none at all. Moreover, as will be described in greater detail below, the amount and type of movement that the dynamic fixation system permits, can be tailored for individual patients. For example, for patients with better pathologies (e.g., better bone structure), a less stiff system may be desirable to permit additional movement. Likewise, for patients with more degenerate disks, a stiffer system may be desirable to permit less or no movement. As generally understood by one of ordinary skill in the art, the dynamic fixation system may be used to span adjacent vertebrae. Alternatively, multiple constructs may be joined together to span three, or more vertebrae. In addition, as generally understood by one of ordinary skill in the art, it should be understood that bone fixation elements may include, but are not limited to, polyaxial or mono-axial pedicle screws, hooks (both mono-axial and polyaxial), wire, or other fasteners, clamps or implants. The dynamic fixation system is not limited in its use to any particular type of bone fixation element.

Moreover, while the dynamic fixation system will be described as and may generally be used in the spine (for example, in the lumbar, thoracic or cervical regions), those skilled in the art will appreciate that the dynamic fixation system as well as the components thereof may be used for fixation of other parts of the body such as, for example, joints, long bones or bones in the hand, face, feet, etc.

Figure 2:
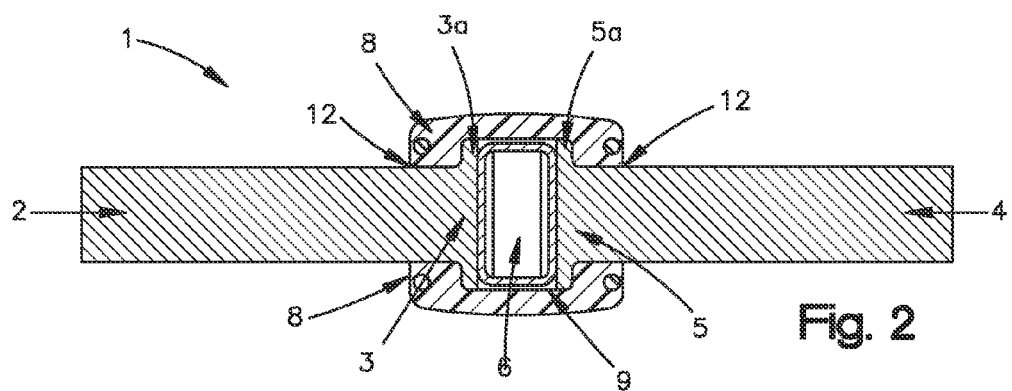
FIG. 2 is a cross-sectional view of the dynamic fixation system of FIG. 1.
Figure 3:
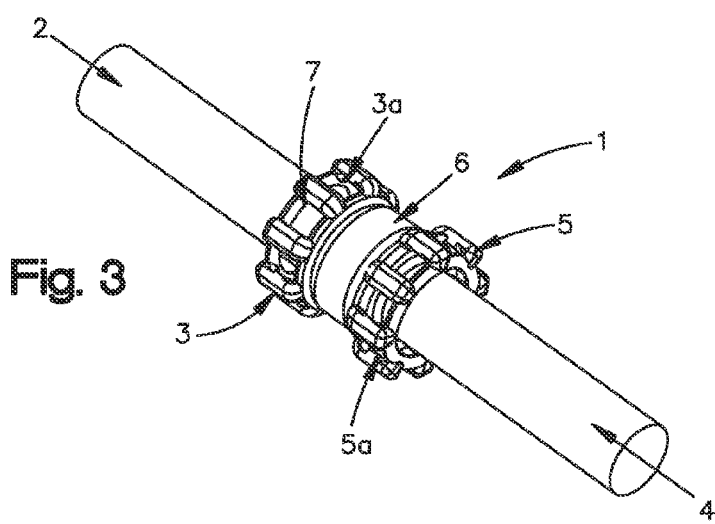
FIG. 3 is a perspective view of the dynamic fixation system of FIG. 1 with the housing removed.

As shown in FIGS. 1-3, the dynamic fixation system 1 may include a first rod 2 having an end portion 3, a second rod 4 having an end portion 5, and a damping component 6 positioned between the end portions 3, 5 of the first and second rods 2, 4. The end portions 3, 5 of the first and second rods 2, 4 may be enlarged end portions, 3a, 5a respectively, for reasons that will become apparent below. The dynamic fixation system 1 may also include a housing 8 spanning the first and second rods 2, 4. The housing 8 may include an inner cavity 9 for receiving and/or encapsulating the damping component 6 and/or the end portions 3, 5, preferably the enlarged end portions 3a, 5a, of the first and second rods 2, 4. The housing 8 may also include one or more openings 12, preferably at least two openings 12, formed on either end thereof, the openings 12 preferably being in communication with the inner cavity 9, so that the ends 3, 5, preferably the enlarged ends 3a, 5a, of the first and second rods 2, 4 may extend therein. In one embodiment, the rods 2, 4 may be slidably received therein, so that the first and second rods 2, 4 may be independently slidably associated with the housing 8. As shown, the openings 12 preferably have a diameter smaller than the diameter of the first and second enlarged ends 3a, 5a to prevent the enlarged ends 3a, 5a of the rods 2, 4 from being pulled out of the housing 8. Alternatively, the rods 2, 4 may be slidably associated with the housing 8 but are prevented from being disassociated therewith by any other means known in the art. Preferably, the enlarged ends 3a, 5a include a plurality of openings 7 (as best shown in FIG. 3), so that the housing 8 can be interwoven into the openings 7 formed in the enlarged ends 3a, 5a of the rods 2, 4.

The damping component 6 may be connected to the first and second rods 2, 4, preferably between the first and second enlarged ends 3a, 5a, by any means known in the art, including, but not limited to, adhesive, welding, clamps, pins, etc. Alternatively, the damping component 6 may be configured so that it is not physically joined or connected to one or both of the rods 2, 4, and in addition thereto may be freely moveable between the first and second rods 2, 4. Preferably, the damping component 6 is injection molded between the first and second rods 2, 4. More preferably, the enlarged ends 3a, 5a include a plurality of openings 7 (as best shown in FIG. 3), so that the damping component 6 can be injection molded through the openings 7. As a result, when the damping component 6 cures and hardens within the openings 7, the damping component 6 will be, at least partially, secured to the ends 3, 5 of the rods 2, 4.

The enlarged ends 3a, 5a may be formed as a separate and independent piece and attached to the rods 2, 4 by any means known in the art including, but not limited to, adhesive, welding, clamps, pins, etc. Preferably, however, the enlarged ends 3a, 5a are integrally formed with the rods 2, 4.

The rods 2, 4 may be sized and configured to be slidably arranged with respect to the housing 8 and with respect to each other. In this manner, the dynamic fixation system 1 is better able to absorb some or all of the movement. The first and second rods 2, 4 may be prevented from rotating with respect to the housing 8 and/or with respect to each other. For example, the rods 2, 4, may be sized and configured to prevent relative rotation by forming the ends 3, 5 of the rods 2, 4 and the openings 12 in the housing 8 with complementary shapes that prevent rotation, such as, for example, square, hexagonal, elliptical, etc. Alternatively, the rods 2, 4 may rotate with respect to one another and with respect to the housing 8.

The housing 8 may be made of a single piece of material or may be two or more pieces of material joined together. In the embodiment where the housing is made of multiple pieces, the pieces may be held together by any means known in the art, including, but not limited to, welding, adhesive, clamps, pins, etc. In addition, metal wires may be woven or inserted into the housing 8, especially the carbon fiber housing, to strengthen the interface between the housing 8 and the first and second rods 2, 4.

As readily understood by one of ordinary skill in the art, in situ, as a patient's vertebrae move, the movement (e.g., translation, articulation, rotation (e.g. twisting), etc.) and associated loads are transferred to the dynamic fixation system 1. As such, the damping component 6 preferably is sized and configured to absorb and transmit the movement and associated loads to the housing 8. The housing 8 preferably is sized and configured to absorb and transmit the movement and associated loads to the rods 2, 4. That is, in situ, as the attached vertebrae move, the movement and associated loads are transferred from the attached vertebrae to the rods 2, 4 via the bone fixation elements, from the rods 2, 4 to the damping component 6, from the damping component 6 to the housing 8, and from the housing 8 back to the rods 2, 4. Thus, in combination, the damping component 6 and housing 8 are preferably sized and configured to absorb, at least partially or wholly, the transferred loads, including but not limited to the translational, articulation, rotational (e.g. twisting), etc. In this manner, the dynamic fixation system enables the attached vertebrae to move with respect to one another.

The viscoelastic damping properties of the dynamic fixation system 1 may be determined by the properties of the damping component 6 superimposed with the elastic properties of the housing 8. For example, the dynamic fixation system 1 may have different stiffnesses based on the properties of the selected damping component 6 and housing 8. Moreover, the damping properties of the dynamic fixation system 1 may be adjusted to match patterns of movements for different patients and for different patient's pathologies.

In an alternate embodiment, as shown in FIGS. 4-7, the dynamic fixation system 20 may include a first rod 22 having an end portion 24, a second rod 26 having an end portion 28, and a damping component 30 positioned between the end portions 24, 28 of the first and second rods 22, 26. As shown, the end of one of the first and second rods 22, 26 (shown as 26) may include an arcuate end portion 28a such as, for example, a spherical or ball-like end portion. The end portion 28 may contact the end of the other rod 22, 26 (shown as 22). The end portion 24 of rod 22 may be in the form of an enlarged end portion 24a, preferably in the form of a housing or cage 31. The housing or cage 31 may be sized and configured to receive the end portion 28, preferably the arcuate end portion 28a, of the rod 26 so that the end portion 28, and hence the rod 26, may move (e.g., translate, angulate, rotate (e.g. twist), etc.) with respect to the housing or cage 31, and hence with respect to the rod 22.

The housing 31 may also include one or more slots 36, the slots 36 being sized and configured to receive one or more tabs 34 formed on the end portion 28. As will be readily understood by one of ordinary skill in the art, the incorporation of the tabs 34 formed on the end portion 28 and the slots 36 formed in the housing 31 act to limit movement of the first rod 22 with respect to the second rod 26. In particular, the incorporation of the tabs 34 and the slots 36 act to limit rotation (e.g., twisting) of the first rod 22 with respect to the second rod 26. That is, preferably the slot 36 is sized and configured to be larger than the tab 34 to permit some rotation of the tab 34 with respect to the slot 36, and hence the first rod 22 with respect to the second rod 26. In addition, the length and width of the slot 36 and/or tab 34 controls the amount of distance, that the first and second rods 22, 26 can move with respect to one another, and hence controls the amount of deformation between the first and second rods 22, 26.

The housing 31 may be integrally formed with the first or second rod 22, 26, or may be a separate and independent piece and attached thereto. Similarly, the end portion 28 and/or the tabs 34 may be integrally formed with the other of the first or second rod 22, 26 or may be a separate and independent piece and attached thereto, for example, as will be described in connection with FIGS. 8-11 below.

The damping component 30 may be located in-between the housing 31 and the end portion 28. As shown, the housing 31 may include a plurality of holes 32 dispersed around the periphery of the housing 31 to allow the damping component 30 to be injected into the housing 31. In this manner, as the damping component 30 cures and hardens, the damping component 30 may fill the holes 32, which in turn may assist in keeping the damping component 30 from disengaging from the housing 31. Additionally, the damping component 30 may be injection molded around and/or over the housing 31. In this manner the damping component 30 may occupy the space formed in the housing 31, the space formed by the holes 32, and form over the housing 31. Alternatively and/or additionally, as best shown in FIG. 13, one or both of the rods 42, 46 may include a passageway 54 formed therein, through which the damping component 30 may be injected into the housing 51. In such a configuration, the damping component 30 may exit through holes (not shown), for example, in the end portion 28 of the rod 26, to fill the housing 31, thereby encapsulating the end portion 28 in the housing 31. In this manner, as the damping component 30 cures and hardens, the damping component 30 may fill the through holes (not shown), which in turn may assist in keeping the damping component 30 from disengaging from the end portion 28.

In situ, as the attached vertebrae move, the movement and the associated loads are transferred from the vertebrae to the rods 22, 26 via the bone fixation elements, from the rods 22, 26 to the damping component 30, and from the damping component 30 back to the rods 22, 26. In this manner, the dynamic fixation system permits the attached vertebrae to move with respect to one another. The combination of the moveable rods 22, 26 and the damping component 30 may absorb some or all of the movement (e.g., translation, articulation, rotational (e.g., twisting), etc.) and associated loads. In addition, as previously described above, the slot 36 is sized and configured to be larger than the tab 34 in order to permit the tab 34 to move with respect to the slot 36, and hence the first rod 22 to move with respect to the second rod 26. The slots 36 and tabs 34 being sized and configured to control and/or limit the amount and type of movement. The damping component 30 may also prevent the end portion 28 of the rod 26 from being separated (e.g., being pulled out) of the housing 31 formed on the end of the rod 22.

Alternatively, as previously mentioned, the tabs formed on the end portion of the rod may be formed as a separate and independent piece from the rod. As shown in FIGS. 8-11, the housing or cage 31 formed on the end of the rod 22 may include an end cap 37 integrally formed therewith. The end cap 37 may include a sleeve 38 that is large enough to receive the second rod 26, preferably the end portion 28 of rod 26 so that once the end portion 28 of rod 22 is inserted through the sleeve 38 formed in the end cap 37 and into the housing or cage 31, a bolt 34*a* may be inserted through the slot 36 formed in the housing 31 and into a hole 29 formed in the end portion 28 of rod 26. The bolt 34*a* preferably being larger than the diameter of the sleeve 38 so that the second rod 26 is prevented from being separated (e.g., pulled out) from the first rod 22. By way of an example, as shown in FIG. 11*a*, the sleeve 38 formed in the end cap 37 of the housing 31 may include an elliptical opening 38*a* so that the end portion 28, shown as an arcuate end portion 28*a*, of rod 26 can be diagonally or angularly inserted into the elliptical opening 38*a* in a key-type arrangement. Thereafter, once the first and second rods 22, 26 are aligned so that their longitudinal axis are substantially parallel, the end portion 28 will be prevented from escaping through the elliptical opening 38*a*. Alternatively, the end portion 38 may be sized and configured to snap-fit into the sleeve 38. Alternatively, the end cap 37 may be formed as a separate piece and be connected to the housing 31 by any means known in the art, including but not limited to, adhesive, welding, clamps, pins, mechanically fastened including, but not limited to, a bayonet-type connection, threaded engagement, snap-fit connection, etc.

The end cap 37 better ensures that the first and second rods 22, 26 will not become separated (e.g., pulled out) from one another.

Similar to the dynamic fixation system 20 described above, the dynamic fixation system 40, as shown in FIGS. 12-14, may include a first rod 42 having an end portion 44, a second rod 46 having an end portion 48, and a damping component 50 positioned between the end portions 44, 48 of the first and second rods 42, 46. As shown, the end of one of the first and second rods 42, 46 (shown as 46) may have an arcuate end portion 48*a* such as, for example, a spherical or ball-like end portion. The end portion 48 may contact the end of the other rod 42, 46 (shown as 42). The other rod 46 may include an enlarged end portion 44*a*, preferably in the form of a housing or cage 51. Preferably, the housing or cage 51 may be sized and configured to receive the end portion 48, preferably the arcuate end portion 48*a*, of the rod 46 so that the end portion 48, and hence rod 46, may move (e.g., translate, angulate, rotate (e.g. twist), etc.) with respect to the cage 51, and hence with respect to the rod 42.

The housing 51 may be integrally formed with the first or second rod 42, 46, or may be a separate and independent piece and attached thereto. Similarly, the end portion 48 may be integrally formed with the other of the first or second rod 42, 46, or may be a separate and independent piece and attached thereto.

The damping component 50 may be located in-between the housing 51 and the end portion 48. As shown, the housing 51 may include a plurality of holes 52 dispersed around the periphery of the housing 51 to allow the damping component 50 to be injected into the housing 51. As the damping component 50 cures and hardens, the damping component 50 may fill the holes 52, which in turn may assist in keeping the damping component 50 from being separated (e.g., being pulled out) from the housing 51. Additionally, the damping component 50 may be injection molded over and/or around the housing 51. In this manner the damping component 50 may occupy the space formed in the housing 51, the space formed by the holes 52, and form over the housing 51. Alternatively and/or additionally, as best shown in FIG. 13, one or both of the rods 42, 46 may have a passageway 54 therethrough, through which the damping component 50 may be injected into the housing 51. In such a configuration, the damping component 50 may exit through holes 53, for example, in the end portion 48 of the rod 46, to fill the housing 51, thereby encapsulating the end portion 48 in the housing 51. As the damping component 50 cures and hardens, the damping component 50 may fill the through holes 53, which in turn may assist in keeping the damping component 50 from being separated (e.g., being pulled out) from the end portion 48.

In situ, as the attached vertebrae move, the movement and the associated loads are transferred from the vertebrae to the rods 42, 46 via the bone fixation elements, from the rods 42, 46 to the damping component 50, and from the damping component 50 back to the rods 42, 46. In this manner, the dynamic fixation system enables the attached vertebrae to move (e.g. translate, articulate, rotate (e.g. twist), etc.) with respect to one another. The combination of the moveable rods 42, 46 and the damping component 50 may absorb some or all of the movement and associated loads. In addition, as will be readily understood by one of ordinary skill in the art, the configuration of the dynamic fixation system 40 may allow for additional rotation as compared to the dynamic fixation system 20 of FIGS. 8-11 as there is no mechanism (e.g. slots 36 and tabs 34) to restrain movement of the second rod 46 within the housing 51. The damping component 50 may also prevent the end portion 48 of the rod 46 from being separated (e.g., being pulled out) of the housing 51 formed on the end of the rod 42.

Alternatively and/or additionally, as shown in FIGS. 15-17, the dynamic fixation system 40 may also include a locking cap 57 to provide additional tensional stiffness, and to provide additional protection to prevent the rod 46 from being separated (e.g., being pulled out) from the housing 51. As shown, the locking cap 57 may include a sleeve 58 that is large enough to receive the second rod 46 but which is sized smaller than the arcuate end portion 48a so that the second rod 46 may not disengage or separate from the first rod 42. The locking cap 57 may be connected to the housing 51 by any means known in the art, including, but not limited to, adhesive, welding, clamps, pins, mechanically fastened including, but not limited to, a bayonet-type connection, threaded engagement, snap-fit connection, etc.

As a result of the generally large surface area between the damping component 50 and the rods 42, 46, preferably between the damping component 50 and the end portion 48 and between the damping component 50 and the housing 51, the dynamic fixation system 40 is capable of absorbing the anticipated loads.

Figure 19:
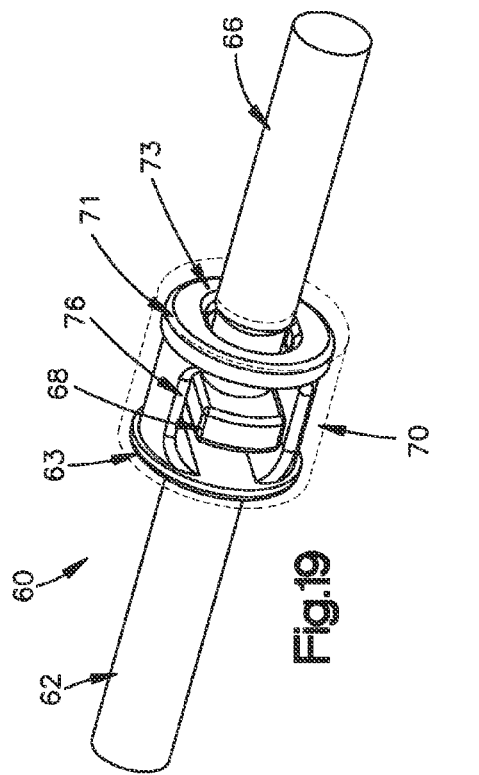
FIG. 19 is a perspective view of the dynamic fixation system of FIG. 18.
Figure 18:
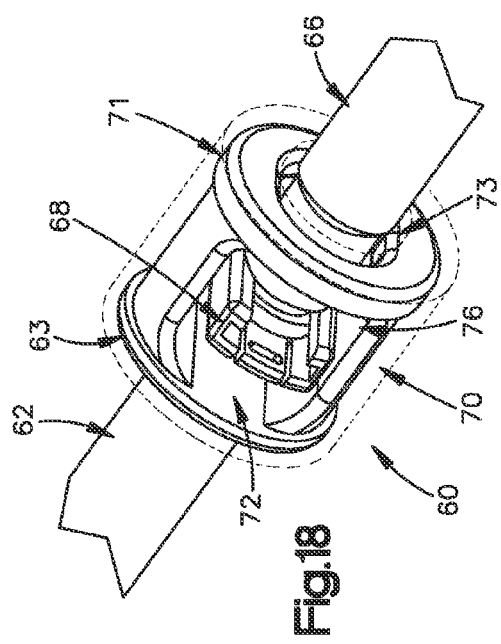
FIG. 18 is a perspective view of an alternative embodiment of a dynamic fixation system.
Figure 20:
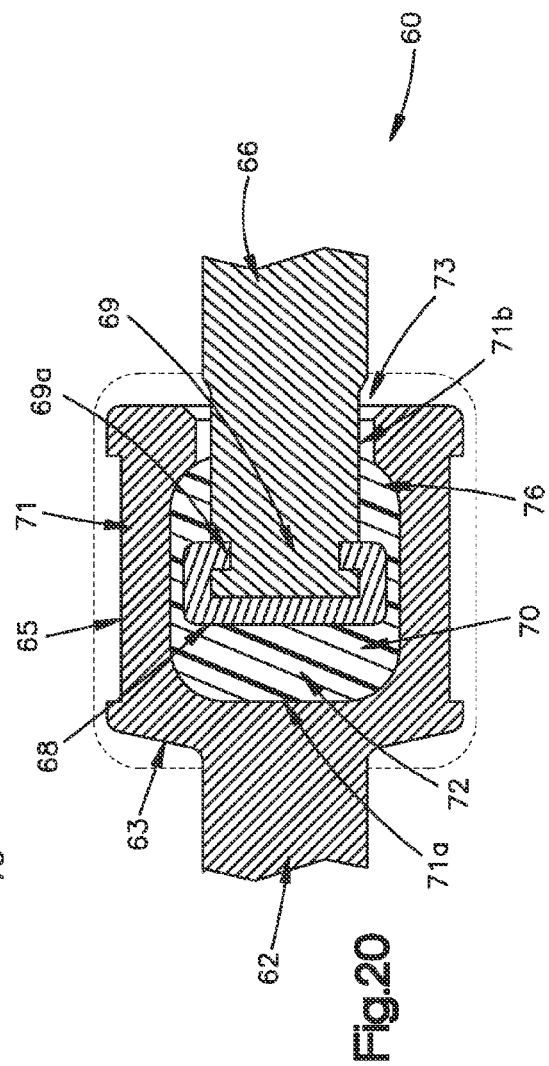
FIG. 20 is a cross-sectional view of the dynamic fixation system of FIG. 18.

In another embodiment, as shown in FIGS. 18-20, the dynamic fixation system 60 may include a first rod 62 having an end portion 63, a second rod 66 having an end portion 69, and a damping component 70 positioned between the first and second rods 62, 66. As shown, one of the end portions 63, 69 of the first and second rods 62, 66 (shown as rod 62) may be in the form of an enlarged end portion 65, preferably in the form of a housing 71. The housing 71 may include an inner cavity 72, an opening 73 formed opposite the rod 62, and a window 76 formed on a side thereof. The opening 73 and the window 76 preferably may be in communication with the inner cavity 72. Preferably, the opening 73 may be sized and configured to receive the end portion 69 of the rod 66 so that the end portion 69, and hence rod 66, may move (e.g., translate, angulate, rotate (e.g. twist), etc.) with respect to the housing 71, and hence with respect to the rod 62. As shown, a plate 68 may be operably connected to the end portion 69 of the rod 66. As previously stated, the housing 71 may also include a window 76 formed on a side thereof, the window 76 being sized and configured to enable the plate 68 to be inserted into the housing 71 so that it may engage the end portion 69 of the rod 66 after the rod 66 has been inserted into the opening 73.

The plate 68 may be connected to the end portion 69 of the rod 66 by any means known in the art, including, but not limited to, adhesive, welding, clamps, pins, mechanically fastened including, but not limited to, a bayonet-type connection, threaded engagement, snap-fit connection, etc. Preferably, as shown, the end portion 69 of the rod 66 includes a circumferential notch 69a for slidably receiving the plate 68. The opening 73 preferably is sized and configured to be large enough to receive the second rod 66 but smaller than the plate 68 so that the second rod 66 may not disengage or separate from the first rod 62.

The shape and size of the plate 68 in combination with the window 76 may allow the dynamic fixation system 60 to bend (e.g., the rods 62, 66 may articulate with respect to one another). The size and shape of the plate 68 in combination with the window 76 may also be chosen in order to provide certain damping characteristics. For example, changing the size and/or shape of the plate 68 and/or of the window 76 may affect the amount the rods 62, 66 may move with respect to one another. In addition, the shape of the plate 68 and/or window 76 may also be chosen to prevent the rods 62, 66 from rotating with respect to one another (e.g., the shape may only allow for axial movement and/or angulation in a single plane).

The housing 71 may be integrally formed with the first or second rod 62, 66, or may be a separate and independent piece and attached thereto. Similarly, the end portion 69 may be integrally formed with the other of the first or second rod 62, 66, or may be a separate and independent piece and attached thereto. The plate 68 may be made of, for example, metal. Those skilled in the art will appreciate that other materials for the plate 68 may be used so long as the plate 68 can withstand the anticipated forces (e.g., shear, compression, rotational forces) exerted on the plate 68 when in the body.

The dynamic fixation system 60 may also include a damping component 70 located in-between the end portions 63, 69 of the first and second rods 62, 66, preferably in-between the housing 71 and the plate 68. The damping component 70 may be injected through the window 76. The damping component 70 may be injected above the plate 68 so that the damping component 70 resides in-between one end 71a of the housing 71 and the plate 68 and/or below the plate 68 so that the damping component 70 resides in-between the other end 71b of the housing 71 and the plate 68. Preferably, the plate 68 may be connected to the end portion 69 of the rod 66 in the inner cavity 72 of the housing 71, and the damping component 70 may be injection molded into the inner cavity 72 to substantially fill the inner cavity 72, including the window 76. Additionally, the damping component 70 may be injection molded over and/or around the housing 71. In this manner, the damping component 70 may occupy the space formed in the housing 71, the space formed by the window 76, and form over the housing 185.

In situ, as the attached vertebrae move, the movement and the associated loads are transferred from the vertebrae to the rods 62, 66 via the bone fixation elements, from the rods 62, 66 to the damping component 70, and from the damping component 70 back to the rods 62, 66. In this manner, the dynamic fixation system 60 enables the attached vertebrae to move (e.g. translate, articulate, rotate (e.g. twist), etc.) with respect to one another. The combination of the moveable rods 62, 66 and the damping component 70 may absorb and transfer some or all of the movement and associated loads. In addition, the plate 68 attached to the end portion 69 may restrict the rod's 66 ability to move (e.g. translate, articulate, rotate (e.g. twist), etc.) with respect to the other rod 62. That is, for example, the interaction between the plate 68 and the window 76 formed in the housing 71 may prevent rotation (e.g., twisting) of one rod 62 with respect to the other rod 66. In addition, it may only permit angulation of the rods in a single plane. The damping component 70 may also prevent the end portion 68 of the rod 66 from being separated (e.g., being pulled out) of the housing 71 formed on the end of the rod 62.

As a result of the generally large surface area between the damping component 70 and the rods 62, 66, preferably between the damping component 70 and the plate 68 and between the damping component 70 and the housing 71, the dynamic fixation system 60 is capable of absorbing the anticipated loads.

In an alternative embodiment as shown in FIGS. 21-23, the damping component 70 may be replaced by a damping mechanism (shown as one or more springs 78). As shown, preferably the one or more springs 78 may be located within the housing 71 formed on the end 63 of the rod 62. As shown, preferably, the dynamic fixation system includes at least two springs, 78a, 78b, one of the springs 78a residing in-between one end 71a of the housing 71 and the plate 68 while the other spring 78b resides in-between the other end 71b of the housing 71 and the plate 68. As will be appreciated by one of ordinary skill in the art, the dynamic fixation system 60 may only include one of said springs 78 or may include additional springs 78.

The dynamic fixation system 60 may also include a guiding feature to assist in axially guiding the rods 62, 66 with respect to one another. That is, as best shown in FIG. 23, one of the first and second rods 62, 66 (shown as 66) may include a projection 80 extending from an end 69 thereof, and the other rod 62, 66 (shown as 62) may include a recess 82 which may be sized and configured to receive the projection 80 so that the projection 80 is slidably moveable within the recess 82 as compression/tension is exerted on the dynamic fixation system 70. As shown, in use, preferably one of the springs 78b may be sized and configured to coil around the rod 66 while the other spring 78a may be sized and configured to coil around the projection 80. In this manner, the springs 78 are prevented from being expelled out of the housing 71.

The projection 80 may be integrally formed with the first or second rod 62, 66, or may be a separate and independent piece and attached thereto. The plate 68 may include a slot (not shown) for receiving the projection 80 therethrough. Alternatively, the plate 68 may be replaced by one or more partial plates 81, such that each partial plate 81 may operably connect to a portion of the notched end 69a.

Additionally, the dynamic fixation system may also include a damping component 85 in combination with the damping mechanism 78. The damping component 85 may be located in-between the end portions 63, 69 of the first and second rods 62, 66, preferably in-between the housing 71 and the plate 68. The damping component 85 may be injected through the window 76. The damping component 85 may be injected above the plate 68 so that the damping component 85 resides in-between one end 71a of the housing 71 and the plate 68 and/or below the plate 68 so that the damping component 85 resides in-between the other end 71b of the housing 71 and the plate 68. Preferably, the plate 68 may be connected to the end portion 69 of the rod 66 in the inner cavity 72 of the housing 71, and the damping component 85 may be injection molded into the inner cavity 72 to substantially fill the inner cavity 72, including the window 76. Additionally, the damping component 85 may be injection molded over and/or around the housing 71. In this manner, the damping component 85 may occupy the space formed in the housing 71, the space formed by the window 76, and form over the housing 71. Alternatively and/or additionally, as previously described in connection with FIG. 13, one or both of the rods 62, 66 may include a passageway (not shown) formed therein, through which the damping component 85 may be injected into the housing 71. In such a configuration, the damping component 85 may exit through holes (not shown) formed on one of the first and second rods 62, 66 to fill the housing 71, thereby encapsulating the end portion 69 and/or plate 81 in the housing 71.

As shown in FIGS. 24 and 25, an alternative dynamic fixation system 90 may include a first rod 92 having an end portion 93, a second rod 96 having an end portion 97, and a damping mechanism 100 positioned between the end portions 93, 97 of the first and second rods 92, 96. As shown, the end portion 97 of one of the first and second rods 92, 96 (shown as 96) may be in the form of an enlarged end cap 98 integrally formed on the end of the rod 96. Alternatively, the enlarged end cap 98 may be formed as a separate and independent piece and attached thereto. As previously described in connection with dynamic fixation system 60, one of the end portions 93 of the first and second rods 92, 96 (shown as 92) may be in the form of an enlarged end portion 95, preferably in the form of a housing 101. Preferably, the housing 101 may be sized and configured to receive the enlarged end cap 98 of the rod 96 so that the enlarged end cap 98, and hence rod 96, may move (e.g., translate, angulate, rotate (e.g. twist), etc.) with respect to the housing 101, and hence with respect to the rod 92.

The dynamic fixation system 90 may also include a locking cap 108 to prevent the damping mechanism 100 and/or rod 96 from being separated (e.g., being pulled out) from the housing 101. The locking cap 108 may include a sleeve 110 that is large enough to receive the rod 96 but which is sized smaller than the enlarged end cap 98 so that the second rod 96 may not be separated (e.g., pulled out) from the first rod 92. The locking cap 108 may be connected to the housing 101 by any means known in the art, including, but not limited to, adhesive, welding, clamps, pins, mechanically fastened including, but not limited to, a bayonet-type connection, threading engagement, snap-fit connection, etc. Alternatively, the locking cap 108 may be integrally formed with the housing 101. In this configuration, the enlarged end cap 98 and sleeve 110 are sized and configured so that the end portion 97 of the rod 96 can be inserted into the housing 101 via the sleeve 110 in a snap-fit or key type arrangement.

The damping mechanism 100 may be in the form of one or more damping mechanisms 103. As shown, the damping mechanism 100 may include first and second damping mechanisms 104, 106 located in-between the housing 101 and the enlarged end cap 98. In this embodiment, all the components may be made of the same or different types of metal. As shown, the first damping mechanism 104 may be, for example, a washer spring, and the second damping mechanism 106 may be, for example, a coil spring. Different springs may be used to adjust the mechanism 100 to different patient needs.

Preferably, the first damping mechanism 104 is located in-between one end 101a of the housing 101 and the end cap 98 and the second damping mechanism 106 is located between the other end 101b of the housing 101 and the end cap 98.

Additionally, the dynamic fixation system 90 may also include a damping component 102 in combination with the damping mechanism 100. The damping component 102 may be located in-between the end portions 93, 97 of the first and second rods 92, 96, preferably in-between the housing 101 and the locking cap 108 so that the inner cavity of the housing 101 is substantially filled. The damping component 102 may be injected into the inner cavity of the housing by any means known in the art. Additionally, the damping component 102 may be injection molded over and/or around the housing 101. In this manner, the damping component 102 may occupy the space formed in the housing 101 and form over the housing 101. Alternatively and/or additionally, as previously described in connection with FIG. 13, one or both of the rods 92, 96 may include a passageway (not shown) formed therein, through which the damping component 102 may be injected into the housing 101. In such a configuration, the damping component 102 may exit through holes (not shown) formed on one of the first and second rods 92, 96 to fill the housing 101, thereby encapsulating the end portion 97 within the housing 101.

In situ, as the attached vertebrae move, the movement and the associated loads are transferred from the vertebrae to the rods 92, 96 via the bone fixation elements, from the rods 92, 96 to the damping mechanisms 104, 106 and optional damping component 102, and from the damping mechanisms 104, 106 and optional damping component 102 back to the rods 92, 96. In this manner, the dynamic fixation system 90 enables the attached vertebrae to move (e.g., translate, articulate, rotate (e.g. twist), etc.) with respect to one another. The combination of the moveable rods 92, 96 and the damping mechanisms 104, 106 may absorb and transfer some or all of the movement and associated loads. The damping mechanism 106 may also prevent the end portion 98 of the rod 96 from being separated (e.g., being pulled out) of the housing 101 formed on the end of the rod 92.

As shown in FIG. 26, an alternate embodiment of the dynamic fixation system 140 may include a first rod 142 having an end portion 143, a second rod 145 having an end portion 146, and a damping mechanism 148 joining the first and second rods 142, 145. The damping mechanism 148 may be in the form of a damper 149, preferably a collapsible damper similar to a bellows. As shown in FIG. 27, the end portions 143, 146 of rods 142, 145 may be in the form of enlarged end portions 144, 147. Moreover, one of the rods 142, 145 (shown as rod 145) may include a projection 150 extending therefrom, while the other of the rods 142, 145 (shown as rod 142) includes a recess 151 formed therein, the recess 151 being sized and configured to slidably receive the projection 150 so that the first rod 142 may translate with respect to the second rod 145. The damper 149 preferably includes a central throughbore 149a extending completely therethrough. The central throughbore 149a being sized and configured to receive the projection 150 so that the projection 150 formed in rod 145 may extend completely through the damper 149 and into the recess 151 formed in rod 142.

The projection 150 and the recess 151 may also be sized and configured to permit the rods 142, 145 to angulate and/or rotate with respect to one another. For example, the projection 150 may additionally and/or alternatively include an enlarged end portion 152, preferably an arcuate end portion 153, formed on the end of the projection 150. The enlarged end portion 152 preferably has a diameter greater than that of the projection 150, so that the enlarged end portion 152 may be secured within the recess 151 by any means known in the art, including, but not limited to, snap-fitting, locking caps, etc. so that the second rod 145 may not be separated (e.g., pulled out) from the first rod 142. As previously described above in connection with FIG. 11a, the recess 151 may be formed with an elliptical opening (not shown) for receiving the arcuate end portion 153 in a key-type arrangement.

The projection 150 may be integrally formed with the first or second rod 142, 145, or may be a separate and independent piece and attached thereto. The enlarged end portion 152 may be integrally formed with the projection 150, or may be a separate and independent piece and attached thereto.

The damper 149 may be connected to the first and second rods 142, 145, preferably between the first and second end portions 143, 146, by any means known in the art, including, but not limited to, adhesive, welding, clamps, pins, etc. Alternatively, the damper 149 may be configured so that it is not physically joined or connected to one or both of the rods 142, 145, and in addition thereto may be freely moveable between the first and second rods 142, 145. As shown, the damper 149 may have an hourglass shape. Alternatively, the damper 149 may be formed as one or more diametrically enlarged beads (not shown), which may be connected to one another in a series.

As shown in FIG. 28, the ends 143, 146 of the rods 142, 145 may include a notch 160 around the circumference thereof for receiving the ends 161, 162 of the damper 149 therein. In this embodiment, the damper 149 may include a solid central portion 170 located between two bulbous portions 175 since the central throughbore 149a is not required. The damper 149 enables the first and second rods 142, 145 to move (e.g., translate, angulate, rotate (e.g. twist), etc.) with respect to one another. That is, in use, the damper 149 acts like a spring element facilitating absorption and/or transmission of the movement and the associated loads.

The damper 149 may be manufactured by any biocompatible material known in the art including but not limited to cobalt chromium, stainless steel, titanium, titanium alloys, plastics, carbon fiber reinforced matrix, carbon fiber reinforced plastic, polymers including but no limited to polyetheretherketone (PEEK), polyetherketoneketone (PEKK), polyetherketone (PEK), etc.

Alternatively and/or in addition, the damper 149 may be partially or completely filled with an injection molded damping component 155 (as previously described). However, those skilled in the art will appreciate that the damper 149 may be hollow, in which case the damping mechanism 148 relies on the stiffness and spring properties of the damper 149 for damping.

In situ, as the attached vertebrae move, the movement and the associated loads are transferred from the vertebrae to the rods 142, 145 via the bone fixation elements, from the rods 142, 145 to the damper 149, and from the damper 149 back to the rods 142, 145. In this manner, the dynamic fixation system 140 enables the attached vertebrae to move (e.g. translate, articulate, rotate (e.g. twist), etc.) with respect to one another. The combination of the moveable rods 142, 145 and the damper 149 may absorb some or all of the movement and associated loads. The damper 149 may also assist in preventing the second rod 145 from being separated (e.g., being pulled out) from the first rod 142.

As shown in FIGS. 29 and 30, in an alternative embodiment of the dynamic fixation system 180, the dynamic fixation system 180 may include a first rod 182 including an end portion 184 and a second rod 186 including an end portion 188, the end portions 184, 188 of the first and second rods 182, 186 being connected to one another. As shown, the end portion 184, 188 (shown as 184) of one of the first and second rods 182, 186 (shown as 182) may include an enlarged end portion 184a, preferably in the form of a housing or cage 185. The end portion 188 of the other rod 186 may include an enlarged end portion or end cap 188a, preferably sized and configured to match the size and shape of the housing or cage 185. The housing 185 may include a plurality of slots and/or holes 189 so that the housing 185 is flexible. In this manner, the end of one (or both) of the rods 182, 186 can act as a spring-like member which may absorb and/or transmit movement, and the associated loads.

The enlarged end portions 184, 188 may be attached to the rods 182, 186 and to each other by any means known in the art, including, but not limited to, adhesive, welding, clamps, pins, mechanically fastened including, but not limited to, a bayonet-type connection, threaded engagement, snap-fit connection, etc. Alternatively, the end portions 184, 188 may be integrally formed with the rods 182, 186. Preferably, the end portions 184, 186 are prohibit from being separated (e.g., being pulled out) from each other.

Alternatively and/or additionally, the housing 185 may be partially or completely filled with a damping component 190. The damping component 190 may be injected molded into the housing 185 via the plurality of holes 189. In this manner, as the damping component 190 cures and hardens, the damping component 190 may fill the holes 189, which in turn may assist in keeping the damping component 190 from disengaging from the housing 185. Additionally, the damping component 190 may be injection molded over and/or around the housing 185. In this manner, the damping component 190 may occupy the space formed in the housing 185, the space formed by the holes 189, and form over the housing 185. However, those of ordinary skill in the art will appreciate that the housing 185 may be hollow, in which case the dynamic fixation system 180 relies on the stiffness and spring properties of the housing 185 for damping.

In situ, as the attached vertebrae move, the movement and the associated loads are transferred from the vertebrae to the rods 182, 186 via the bone fixation elements, from the rods 182, 186 to the housing 185, from the housing 185 to the optional damping component 190, and from the optional damping component 190 back to the rods 182, 186. In this manner, the dynamic fixation system 140 enables the attached vertebrae to move (e.g. translate, articulate, rotate (e.g. twist), etc.) with respect to one another. The combination of the moveable rods 182, 186 and the housing 185 may absorb some or all of the movement and associated loads. The optional damping component 190 may also assist in the absorption and transmission of the associated loads. The optional damping component 190 may also assist in preventing the second rod 186 from being separated (e.g., being pulled out) from the first rod 182.

As shown in FIGS. 31 and 32, in yet another alternative embodiment, the dynamic fixation system 200 may include a first rod 202 including an end portion 204, a second rod 206 including an end portion 208 and a damping mechanism 209 joining the first and second rods 202, 206. As shown in FIG. 32, the end portions 204, 208 of rods 202, 206 may include enlarged end portions 205, 207. Moreover, one of the rods 202, 206 (shown as rod 206) may include a projection 215 extending therefrom, while the other rod 202, 206 (shown as rod 202) may include a recess 220, the recess 220 being sized and configured to slidably receive the projection 215 so that the first rod 202 may translate with respect to the second rod 206. Alternatively and/or additionally, the projection 215 and recess 220 may also be sized and configured to permit the rods 202, 206 to angulate and/or rotate with respect to one another. For example, the projection 215 may additionally and/or alternatively include an enlarged arcuate end portion 216 for facilitating angulation and/or rotation between the first and second rods 202, 206. The enlarged end portion 216 preferably has a diameter greater than that of the projection 215 so that the enlarged end portion 216 may be secured within the recess 220 by any means known in the art, including, but not limited to, snap-fitting, locking caps, etc. so that the second rod 206 may not be separated (e.g., pulled out) from the first rod 206. As previously described above in connection with FIG. 11a, the recess 220 may be formed with an elliptical opening (not shown) for receiving the arcuate end portion 216 in a key-type arrangement.

The projection 215 may be integrally formed with the first or second rod 202, 206, or may be a separate and independent piece and attached thereto. The enlarged end portion 216 may be integrally formed with the projection 215, or may be a separate and independent piece and attached thereto.

The damping mechanism 209 may be in the form of a spring 210, preferably an S-shaped spring including a first end 211, a second end 212 and an intermediate portion 213 located therebetween. The first and second ends 211, 212 of the S-shaped spring 210 may be connected to the first and second rods 202, 206, preferably between the first and second end portions 204, 208, by any means known in the art, including, but not limited to, adhesive, welding, clamps, pins, etc. Preferably, the first and second end portions 204, 208 each include a circumferential notch 204a, 208a, respectively, for engaging a groove (not shown) formed in the first and second ends 211, 212 of the spring 210. The intermediate portion 213 of the spring 210 preferably includes an opening 213a to enable the projection 215 to extend therethrough so that the projection 215 may extend through the spring 210 and into the recess 220 formed on rod 202.

In situ, as the attached vertebrae move, the movement and the associated loads are transferred from the vertebrae to the rods 202, 206 via the bone fixation elements, from the rods 202, 206 to the spring 210, and from the spring 210 back to the rods 202, 206. In this manner, the dynamic fixation system 200 enables the attached vertebrae to move (e.g. translate, articulate, rotate (e.g. twist), etc.) with respect to one another. The combination of the moveable rods 202, 206 and the spring 210 may absorb some or all of the movement and associated loads.

In addition, the enlarged end portion 216 may be configured to restrict the ability of rods 202, 206 to articulate and/or twist with respect to one another. That is, for example, the enlarged end portion 216 and the recess 220 may have complementary shapes, such as, for example, square, hexagon, etc., thus preventing articulation and/or rotation of the rods 202, 206. The enlarged end portion 216 preferably also assists in preventing the projection 215 from being separated (e.g., being pulled out) from the recess 220 and thus assists in preventing rod 202 from becoming separated from rod 206.

As illustrated in FIGS. 33 and 34, in yet another alternative embodiment, the dynamic fixation system 230 may include a first rod 232 including an end portion 234 and a second rod 236 including an end portion 238. Preferably, the end portions 234, 238 are sized and configured to engage one another. More preferably, one of the end portions 234, 238 is sized and configured to slidably receive the other end portion 234, 238. That is, as shown, the end portion 234, 236 (shown as 234) of one of the first and second rods 232, 236 (shown as 232) may include an enlarged end portion 234a, preferably in the form of a housing or cage 235 while the other end portion (shown as 238) of the other rod (shown as 236) may include an end portion 238, preferably an enlarged end portion 238a. End portion 238 being sized and configured to be received by the housing or cage 235.

The end portions 234, 238 may be integrally formed with the first and second rods 232, 236, respectively, or they may be separate and independent pieces and attached thereto.

The housing 235 may also include a plurality of slots and/or holes 240 so that the housing 235 may be flexible and act as a spring-like member so that it can absorb and transmit movement (e.g., translation, articulation, rotation (e.g. twisting), etc.).

As shown, the housing 235 may also include a pair of openings 241 on either side thereof, the openings 241 being sized and configured to receive a locking bolt 245. Similarly, the end portion 238 may include a through bore 239, the through bore being sized and configured to receive the locking bolt 245 so that, in use, the end portion 238 of rod 236 may be connected to the end portion 234 or rod 232 by the locking bolt 245. The locking bolt 245 being sized and configured to pass through one of the openings 241 formed in the housing 235, through the through bore 239 formed in the end portion 238 and into the other opening 241 formed in the housing 235. The locking bolt 245 may be connected to the housing 235 and/or the end portion 238 by any means known in the art, including, but not limited to, press-fit, adhesive, welding, a bayonet-type connection, threaded engagement, snap-fit connection, etc. The locking bolt 245 may prevent the end portion 238, and hence rod 236, from being separated (e.g., being pulled out) from the housing 235, and hence rod 232. In addition, the locking bolt 245 may act as a pivot, thereby permitting the rod 236 to pivot with respect to the other rod 232. Thus, the rods 232, 236 are permitted to angulate with respect to one another in a single plane.

As will be generally appreciated by one of ordinary skill in the art, the end portions 234, 238 may be sized and configured to control the amount of movement permitted in the dynamic fixation system 230. That is, if the end portion 238 is sized and configured to substantially fill the end portion 234, less movement will be permitted, and vice versa. In this embodiment, all the components may be made of, for example, the same or different types of metal.

In situ, as the attached vertebrae move, the movement and the associated loads are transferred from the vertebrae to the rods 232, 236 via the bone fixation elements, from the rods 232, 236 to the end portions 234, 238, and from the end portions 234, 238 back to the rods 232, 236. In this manner, the dynamic fixation system 230 enables the attached vertebrae to move (e.g. translate, articulate, rotate (e.g. twist), etc.) with respect to one another. The combination of the moveable rods 232, 236 and end portions 234, 238 may absorb some or all of the movement and associated loads. The locking bolt 245 may also prevent the second rod 236 from being separated (e.g., being pulled out) from the first rod 232.

Alternatively and or additionally, as shown in FIGS. 35 and 36, the dynamic fixation system 230 may also include an end sleeve 247 to constrain (e.g., limit) the amount of movement between the first and second rods 232, 236. Thus, the end sleeve 247 generally increases the amount of stiffness in the dynamic fixation system. That is, the end sleeve 247 preferably adds some additional constraints to limit the amount of movement (e.g. articulation, rotation, etc.) between the first and second rods 232, 236. In addition, the end sleeve 247 provides additional protection in preventing the first and second rods 242, 246 from separating. As shown, the rod 232 connects to the flexible damping element (e.g. flexible housing 235) via the end sleeve 247. The end sleeve 247 can be connected to the housing 235 by any means known in the art including but not limited to adhesive, welding, clamps, pins, mechanically fastened including, but not limited to, a bayonet-type connection, threaded engagement, snap-fit connection, etc. As shown, the end sleeve 247 may include a bore 248, preferably a threaded bore for threadably engaging a threaded end portion 249 formed on rod 232. However, as readily understood by one of ordinary skill in the art, the end sleeve 247 may be connected to the rod 232 but any other means known in the art including but not limited to adhesive, welding, clamps, pins, mechanically fastened including, but not limited to, a bayonet-type connection, snap-fit connection, etc.

As shown in FIGS. 37-42, in yet another alternative embodiment, the dynamic fixation system 250 may include a first rod 252, a second rod 256 and a damping mechanism 259 positioned between the first and second rods 252, 256. As shown, the damping mechanism 259 may preferably be in the shape of an S-shaped spring 259a. The damping mechanism 259 enables the first rod 252 to move with respect to the second rod 256 and hence permits the attached vertebrae to move with respect to each other.

The damping mechanism 259 may be integrally formed with one or both of the rods 252, 256. Alternatively, the damping mechanism 259 may be a separate and independent piece and attached thereto. The damping mechanism 259 may be attached to the first and second rods 252, 256 by any means known in the art, including, but not limited to, adhesive, welding, clamps, pins, etc. Preferably, the damping mechanism 259 is integrally formed with both the first and second rods 252, 256.

The dynamic fixation system 250 may also include constraining means for limiting the amount of movement (e.g., translational, articulation, rotational (e.g. twisting), etc.) between the first and second rods 252, 256. As shown in FIGS. 37 and 38, the constraining means may be in the form of one or more bars 268 that may be operatively connected to the first and second rods 252, 256. As shown, the bars 268 may include a first end 272 and a second end 274, the first and second ends 272, 274 each including at least one hole 275. Similarly, the first and second rods 252, 256 may each include a through bore 260, 264, respectively, so that in use, a first and second locking bolt 262, 266 may be inserted into the holes 275 and through bores 260, 264 formed in the bars 268 and rods 252, 256 to secure the bars 268 to the rods 252, 256. The first and/or second through bores 260, 264 preferably are oblong so that axial movement between the bars 268 and the rods 252, 256 is permitted. Alternatively and/or additionally, the holes 275 formed in the bars 268 may be oblong. As will be generally understood by one of ordinary skill in the art, incorporation of the bars 268 may limit the amount of axial movement in-between the first and second rods 252, 256. In addition, incorporation of the bars 268 may limit articulation to only a single plane, and may also limit the amount of articulation between the first and second rods 252, 256. In addition, incorporation of the bars 268 may prevent rotation between the first and second rods 252, 256.

Alternatively, as shown in FIGS. 39 and 40, the constraining means may be in the form of a sleeve 280 that may be operatively connected to the first and second rods 252, 256. As shown, the sleeve 280 may include a first end 282, a second end 284, and a central through bore 285. The central through bore 285 being sized and configured to receive at least a portion of the first rod 252, the second rod 256 and the damping mechanism 259. The first and second ends 282, 284 preferably each include at least one hole 286. Similarly, the first and second rods 252, 256 may each include a through-bore 260, 264 so that in use, first and second locking bolts 262, 266 may be inserted into the holes 285 and through bores 260, 264 formed in the sleeve 280 and rods 252, 256 to secure the sleeve 280 to the rods 252, 256. The first and/or second throughbores 260, 264 may be oblong so as to permit the sleeve 280 to axially move with respect to the first and second rods 252, 256. Alternatively and/or additionally, the holes 285 formed in the sleeve 280 may be oblong. As will be generally understood by one of ordinary skill in the art, incorporation of the sleeve 280 may limit the amount of axial movement in-between the first and second rods 252, 256. In addition, incorporation of the sleeve 280 may limit articulation to only a single plane, and may also limit the amount of articulation between the first and second rods 252, 256. In addition, incorporation of the sleeve 280 may prevent rotation between the first and second rods 252, 256.

Alternatively, as shown in FIGS. 41 and 42, the constraining means, and specifically the sleeve 280, may include projections 305 extending inwardly from the first and second ends 302, 304. The projections 305 being sized and configured to engage circumferential notches 290, 292 formed in the rods 252, 256. Preferably, one or both of the notches 290, 292 may be sized and configured to be wider than the projection 305 received therein so that, as will be generally understood by one of ordinary skill in the art, at least one of the rods 252, 256 is axial moveable with respect to the other of the rods 252, 256 and the sleeve 280. That is, the circumferential notch 290 formed in rod 256 may be wider than the circumferential projection 305 extending from the first end 302 of the sleeve 280 so that the sleeve 280 is slidably associated to the first rod 252 along the width of the notch 290. Additionally and/or alternatively, the notch 292 formed in the rod 252 may be wider than the projection 305 extending from the second end 304 of the sleeve 280 so that the sleeve 280 is slidably associated to the rod 252 along the width of the notch 292. The axial movement of the first and second rods 252, 256 may be constrained as the ends of the notches contact the projections 305 extending from the ends 302, 304 of the sleeve 280.

As will be generally understood by one of ordinary skill in the art, for this embodiment, incorporation of the sleeve 280 may limit the amount of axial movement in-between the first and second rods 252, 256. The sleeve 280 however may or may not limit articulation to only a single plane and may permit rotation between the first and second rods 252, 256. The sleeve 280 may limit the amount of articulation between the first and second rods 252, 256.

The sleeve 280 may be made of a single piece of material or may be two or more pieces of material joined together. In the embodiment where the sleeve 280 is made of multiple pieces, the pieces may be held together by any means known in the art, including, but not limited to, welding, adhesive, clamps, pins, etc. The sleeve 280 may encapsulate the damping mechanism 259.

The dynamic fixation system 250a, 250b may also include a damping component 261 disposed in the space between the sleeve 280 and the damping mechanism 259. Additionally and/or alternatively, the damping component 261 may be injection molded around and/or over the sleeve 280.

In situ, as the attached vertebrae move, the movement and the associated loads are transferred from the vertebrae to the rods 252, 256 via the bone fixation elements, from the rods 252, 256 to the damping mechanism 259 and optionally to the damping component 261, and from the damping mechanism 259 and/or damping component 261 back to the rods 252, 256. In this manner, the dynamic fixation system 250 enables the attached vertebrae to move (e.g. translate, articulate, rotate (e.g. twist), etc.) with respect to one another. The combination of the moveable rods 252, 256, damping mechanism 259 and optional damping component 261, and constraining means may absorb some or all of the movement and associated loads.

As shown in FIG. 43, in an alternative embodiment, the dynamic fixation system 310 may include a first rod 312 having an end portion 314, and a second rod 316 having an end portion 318 and a damping mechanism 320 in-between the first and second rods 312, 316. The damping mechanism 320 may be in the form of a damper 321, preferably an S-shaped spring. As shown, the first and second end portions 314, 318 may include diameters smaller than those of the first and second rods 312, 316. Preferably, the first and second end portions 314, 318 of the first and second rods 312, 316, respectively, include a threaded end portion 315 formed thereon for threadably engaging the damping mechanism 320. Alternatively, the end portions 314, 318 may engage the damping mechanism 320 by any means known in the art including, but not limited to, press-fit, snap-fit, welding, adhesive, clamps, pins, etc.

The dynamic fixation system 310 may also include constraining means for limiting the amount of movement (e.g., translational, articulation, rotational (e.g. twisting), etc.) between the first and second rods 312, 316. As shown, the constraining means may be in the form of a sleeve 330, that may be operatively connected to the first and second rods 312, 316. As shown, the sleeve 330 may include a first end 332, a second end 334, and a central through bore 335. The central through bore 335 being sized and configured to receive at least a portion of the first rod 312, the second rod 316 and the damping mechanism 320. The first and second ends 332, 334 preferably each include at least one hole 333, 336, respectively, for engaging the ends of the first and second rods 312, 316.

The sleeve 330 may be slidably associated with the first and/or second end portions 314, 318 of the first and second rods 312, 316 so that the first and/or second rods 314, 318 may move with respect to the sleeve 330. As will be generally understood by one of ordinary skill in the art, incorporation of the sleeve 330 may limit the amount of axial movement in-between the first and second rods 312, 316 in that the axial movement of the first and second rods 312, 316 may be constrained as the ends 332, 334 of the sleeve 330 come into contact with the wider portions of the first and second rods 312, 316. In addition, incorporation of the sleeve 280 may limit articulation and/or rotation.

The sleeve 330 may be made of a single piece of material or may be two or more pieces of material joined together. In the embodiment where the sleeve 330 is made of multiple pieces, the pieces may be held together by any means known in the art, including, but not limited to, welding, adhesive, clamps, pins, etc.

The dynamic fixation system 310 may also include a damping component 322 disposed in the space between the sleeve 330 and the damping mechanism 320. Additionally and/or alternatively, the damping component 322 may be injection molded around and/or over the sleeve 330.

In situ, as the attached vertebrae move, the movement and the associated loads are transferred from the vertebrae to the rods 312, 316 via the bone fixation elements, from the rods 312, 316 to the damping mechanism 320 and optionally to the damping component 322, and from the damping mechanism 320 and/or damping component 322 back to the rods 312, 316. In this manner, the dynamic fixation system 310 enables the attached vertebrae to move (e.g. translate, articulate, rotate (e.g. twist), etc.) with respect to one another. The combination of the moveable rods 312, 316, damping mechanism 320, optional damping component 322, and constraining means (e.g., sleeve 330) may absorb some or all of the movement and associated loads.

Figure 44:
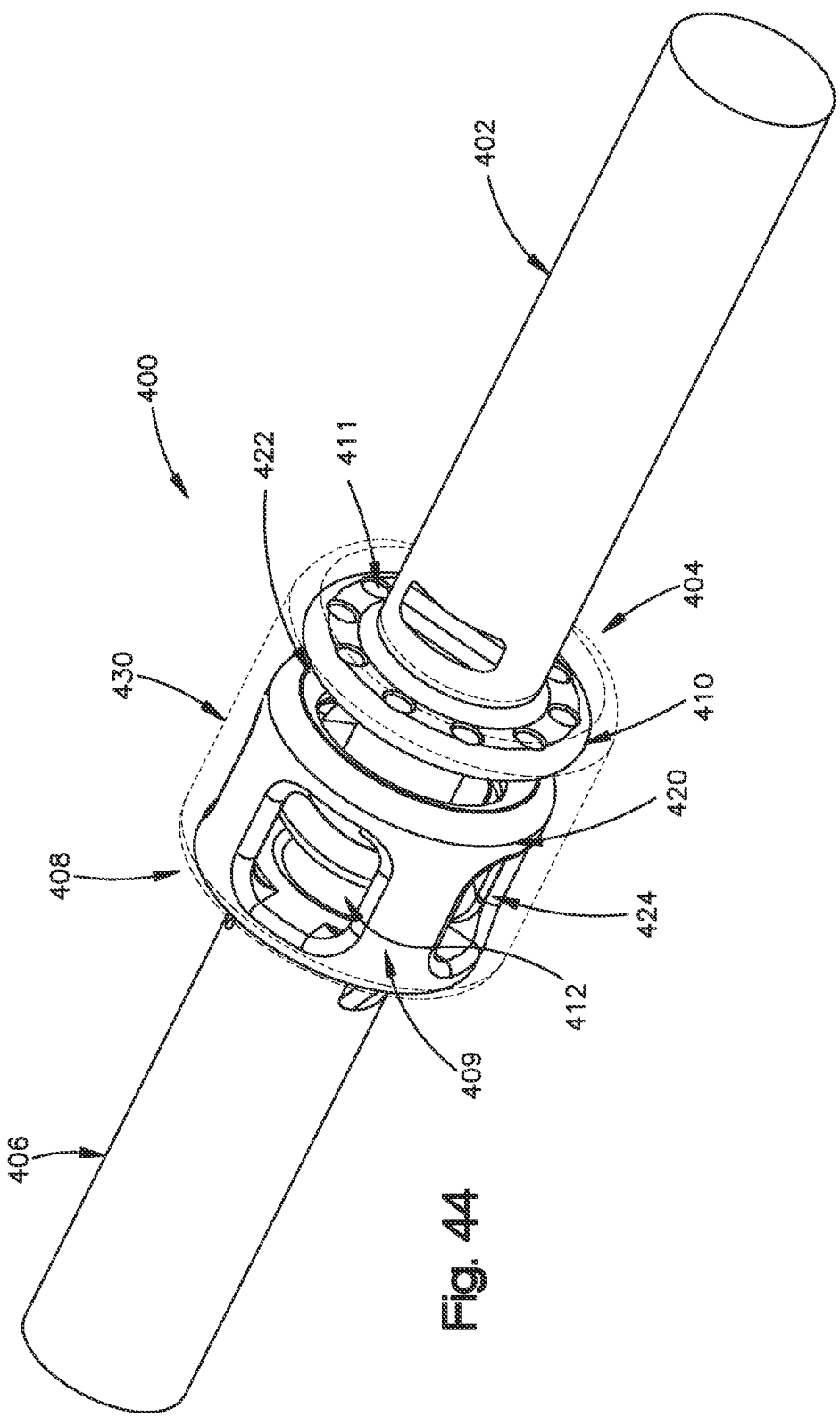
FIG. 44 is a perspective view of an alternative embodiment of a dynamic fixation system.

In an alternate embodiment, as shown in FIG. 44, the dynamic fixation system 400 may include a first rod 402 having an end portion 404, a second rod 406 having an end portion 408, and a damping component 430 positioned between the end portions 404, 408 of the first and second rods 402, 406. As shown, the end of one of the first and second rods 402, 406 (shown as 402) may include a pair of enlarged end portions 410, 412. The end of the other of the first and second rods 402, 406 (shown as 406) may include an enlarged end portion 409, preferably in the form of a housing or cage 420 having an inner cavity 422. The pair of enlarged end portions 410, 412 and the housing or cage 420 are preferably sized and configured so that the inner cavity 422 of the housing 420 receives the outermost enlarged end portion 412 of the rod 402. That is, the outermost enlarged end portion 412 is preferably sized and configured to be received within the inner cavity 422 of the housing 420. As shown, the innermost enlarged end portion 410 may be sized and configured with a diameter that is larger than the diameter of the inner cavity 422 so that the innermost enlarged end portion 410 can not be received within the inner cavity 422 of the housing 420. Alternatively, the innermost enlarged end portion 410 may have a diameter equal to or smaller than the diameter of the outermost enlarged end portion 412 so that the innermost enlarged end portion can be sized and configured to be received within the inner cavity 422 of the housing 420 as well. As will be readily understood by one of ordinary skill in the art, the end of rod 402 may include any number of enlarged end portions (e.g. one, three, four or more).

That is, the end 408 of the second rod 406 preferably includes a housing 420 having an inner cavity 422 and the end 404 of the first rod 402 preferably includes a first diametrically enlarged end portion 412 and a second diametrically enlarged end portion 410. The first diametrically enlarged end portion 412 preferably has a diameter smaller than the inner diameter of the inner cavity 422 of the housing 420 so that the first diametrically enlarged end portion 412 can be slidably received within the inner cavity 422 of the housing 420. The second diametrically enlarged end portion 410 may have a diameter that is smaller than, equal to, or larger than the diameter of the first diametrically enlarged end portion 412. If the second diametrically enlarged end portion 410 has a diameter greater than the diameter of the first diametrically enlarged end portion 412 than the second diametrically enlarged end portion is preferably sized and configured so that it can not be slidably received within the inner cavity 422 of the housing 420. Alternatively, if the second diametrically enlarged end portion 410 is sized and configured with a diameter that is substantially equal to or smaller than the first diametrically enlarged end portion 412 than the second diametrically enlarged end portion 410 may be slidably received within the inner cavity 422 of the housing 420.

Meanwhile, the inner cavity 422 of the housing 420 preferably has an inner diameter that is greater than, at least, the outer diameter of the first diametrically enlarged end portion 412. The diameter of the inner cavity 422 may be smaller than, equal to or larger than the outer diameter of the second diametrically enlarged end portion 410. The inner cavity 422 is preferably sized and configured to slidably receive the first diametrically enlarged end portion 412 and, optionally, may be sized and configured to receive the second diametrically enlarged end portion 410. As shown, the first diametrically enlarged end portion 412 is preferably formed substantially adjacent to the end of the first rod 402 while the second diametrically enlarged end portion 410 is preferably formed somewhere in between the first diametrically enlarged end portion 412 and the other end of the first rod 402.

If the diameter of the innermost enlarged end portion (or the second diametrically enlarged end portion) 410 is sized and configured to be equal to or larger than the diameter of the inner cavity 422, then the innermost enlarged end portion (or the second diametrically enlarged end portion) 410 may act as a stop or stopping mechanism, and thus constrain and/or limit the amount of movement (e.g., translation, articulation, rotation (e.g. twisting), etc.) between the first and second rods 402, 406.

Preferably, as previously stated, the outermost end portion 412 is sized and configured to be slidably received within the inner cavity 422 of the housing 420. More preferably, the outermost end portion 412 is sized and configured to be slidably received within the inner cavity 422 of the housing 420 within very tight tolerances. That is, the inner cavity 422 of the housing 420 is preferably sized and configured to be within a tight tolerance as compared to the enlarged end portion (or the first diametrically enlarged end portion) 412. The inner cavity 422 of the housing 420 thus has a slightly larger diameter as compared to the enlarged end portion (or the first diametrically enlarged end portion) 412 so that a gap (not shown) is formed between the inner cavity 422 and the outer circumference of the enlarged end portion (or the first diametrically enlarged end portion) 412. Therein, when the damping component 430, described in greater detail below, is injected into the inner cavity 422 of the housing 420, the gap formed in between the inner cavity 422 and the outer circumference of the enlarged end portion (or the first diametrically enlarged end portion) 412 may also be filled by the damping component 430. As a result of the tight tolerance and the gap being filled in with the damping component 430, separation of the first rod 402 with respect to the second rod 406 is inhibited and/or prevented. In addition, a certain amount of non-translational movement, such as for example, articulation, rotation, etc. may be permitted.

The housing 420 may be integrally formed with the first or second rod 402, 406 or may be a separate and independent piece and attached thereto. Similarly, the enlarged end portions (or the second and first diametrically enlarged end portions) 410, 412 may be integrally formed with the other of the first or second rod 402, 406 or may be a separate and independent piece and attached thereto. If formed as a separate and independent piece, the housing 420 and the diametrically enlarged end portions 410, 412 may be connected to the rods 402, 406 by any means known in the art including, but not limited to, adhesive, welding, clamps, pins, mechanically fastened including, but not limited to, a bayonet-type connection, threaded engagement, snap-fit connection, etc.

The damping component 430 may be located in-between the housing 420 and the outermost end portion (or the first diametrically enlarged end portion) 412 of the rod 402. As shown, the housing 420 may include a plurality of holes 424 dispersed around the periphery of the housing 420 to allow the damping component 430 to be injected into the housing 420. As the damping component 430 cures and hardens, the damping component 430 may fill the holes 424, which in turn may assist in keeping the damping component 430, and hence the rods 402, 406, from being separated (e.g., being pulled out).

In addition, the innermost enlarged end portion (or the second diametrically enlarged end portion) 410 may include a plurality of openings 411 so that the damping component 430 can be injected through the openings 411. As a result, when the damping component 430 cures and hardens within the openings 411, the damping component 430 will be, at least partially, secured to the ends 404, 408 of the rods 402, 406. Additionally, the damping component 430 may be injected over and/or around the housing 420 and the innermost enlarged end portion (or the second diametrically enlarged end portion) 410. In this manner the damping component 430 may occupy the space formed in the inner cavity 422 of the housing 420, the space formed by the holes 411, 424, and form over the housing 420. Alternatively and/or additionally, as previously described in connection with FIG. 12, one or both of the rods 402, 406 may include a passageway (not shown) therethrough, through which the damping component 430 may be injected into the housing 420. In such a configuration, the damping component 430 may exit through holes (not shown) formed in the end of the rods 402, 406, to fill the housing 420, thereby encapsulating the end portion 412 in the housing 420. As the damping component 430 cures and hardens, the damping component 430 may fill the holes, which in turn may assist in keeping the damping component 430 from being separated (e.g., being pulled out) from the rods 402, 406.

In situ, as the attached vertebrae move, the movement and the associated loads are transferred from the vertebrae to the rods 402, 406 via the bone fixation elements, from the rods 402, 406 to the damping component 430, and from the damping component 430 back to the rods 402, 406. In this manner, the dynamic fixation system 400 enables the attached vertebrae to move (e.g., translation, articulation, rotation (e.g. twisting), etc.) with respect to one another. The combination of the moveable rods 402, 406 and the damping component 430 may absorb some or all of the movement and associated loads. In addition, as readily understood by one of ordinary skill in the art, the enlarged end portions (or the second and first diametrically enlarged end portions) 410, 412 in combination with the damping component 430 may control (e.g. limit) the amount of distance that rod 402 is able to move with respect to rod 406. The damping component 430 may also prevent the enlarged end portions 410, 412 of the rod 402 from being separated (e.g., being pulled out) from the housing 415 formed on the end of the rod 406, and hence prevents rods 402 and 406 from becoming separated with respect to one another.

Figure 45:
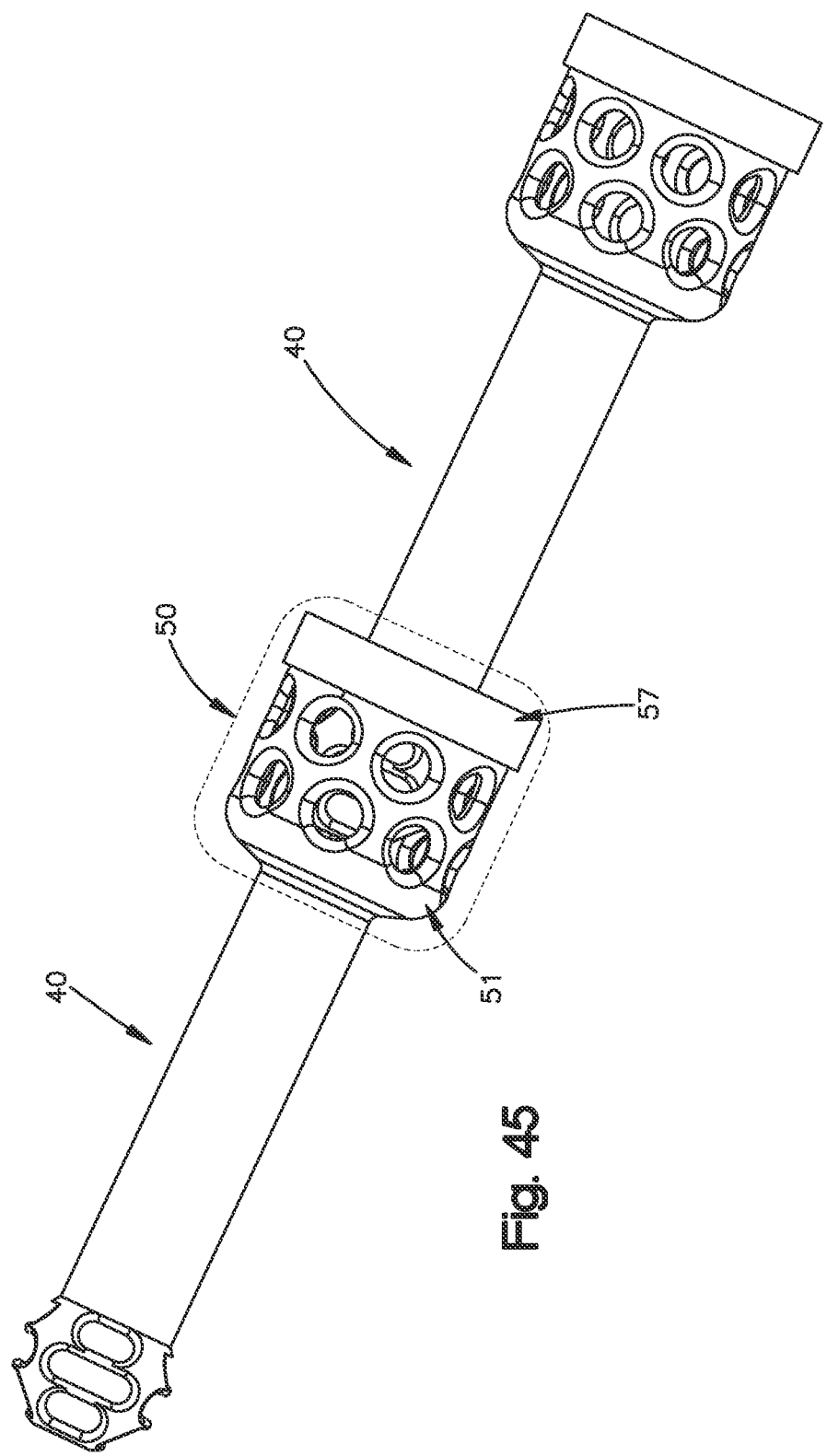
FIG. 45 is a perspective view of a plurality of dynamic fixation systems joined together.
Figure 46:
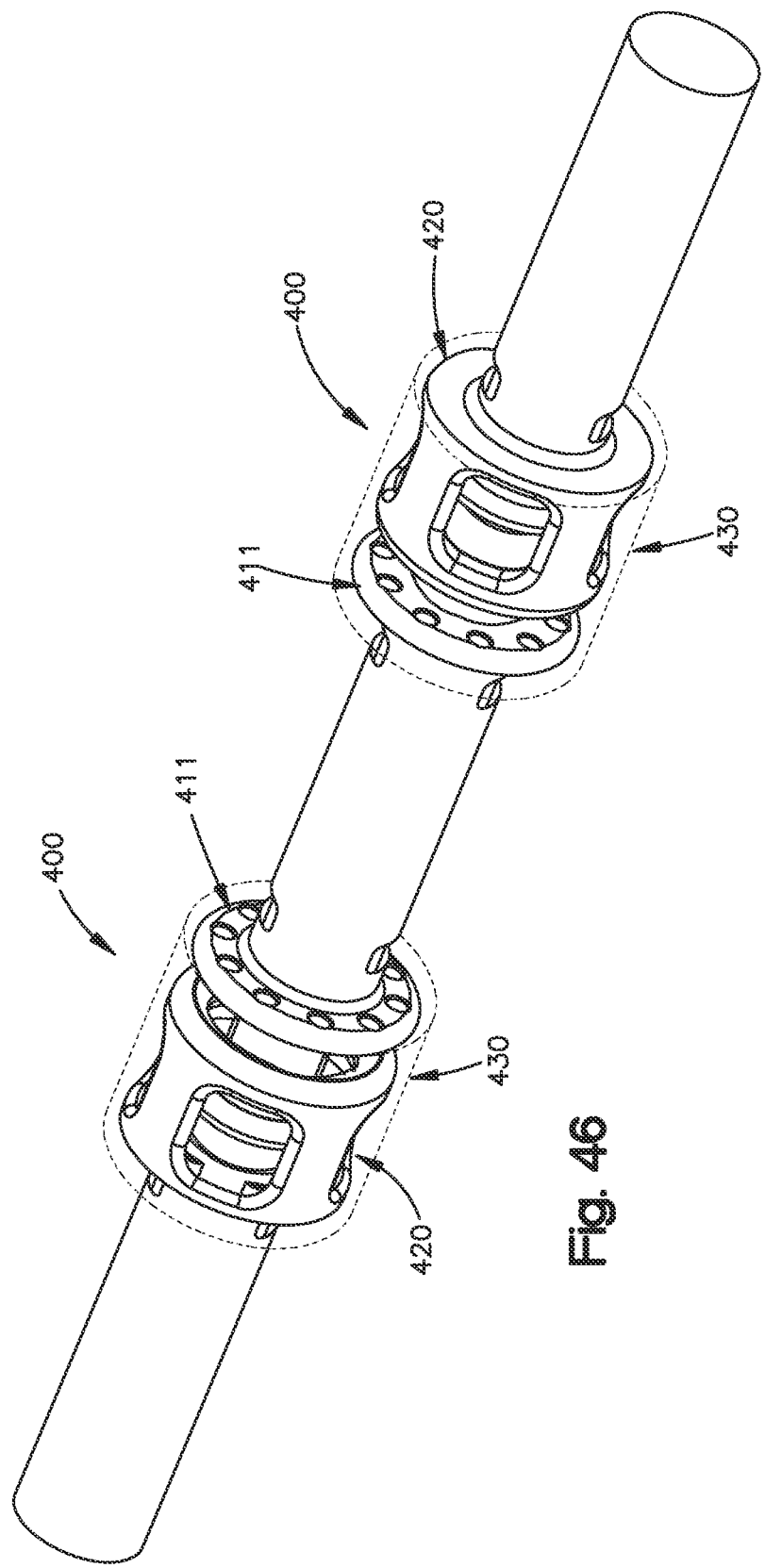
FIG. 46 is another perspective view of a plurality of dynamic fixation systems joined together.

As shown in FIGS. 45 (illustrating dynamic fixation system 40) and 46 (illustrating dynamic fixation system 400), and as previously stated above, each of the dynamic fixation systems can be connected together to form a modular construct so that in use, a plurality of dynamic fixation systems may be connected to a patient's vertebrae via a plurality of bone fixation elements (not shown) to stabilize the vertebrae. As generally understood by one of ordinary skill in the art, two, three or more constructs may be joined together in order to span two, three or more vertebrae. In use, the plurality of dynamic fixation systems are sized and configured to interact with one another to permit relative movement (e.g., translational, articulation, rotational (e.g. twisting), etc.) while being sized and configured to absorb and transmit the necessary loads.

Alternatively and/or additionally, as shown in FIG. 47 (illustrated as dynamic fixation system 400), one or more of the dynamic fixation systems may be connected to a substantially rigid rod 350. The dynamic fixation system and the rigid rod 350 may be connected by any means known in the art. As shown, for example, the rigid rod 350 may include an end portion (shown as a housing 420) for engaging the enlarged end portions 410, 412 of the dynamic fixation system 400. In this manner, combinations of rigid fusion and dynamic fixation can be tailored for individual patients. For example, the dynamic fixation system may be used to treat sections of a patient's spine with less degenerate disk, while the rigid rod 350 may be fixed to sections of a patient's spine that suffer from more degenerate disk. As will be appreciated by those skilled in the art, any or all of the rods described herein may include a curvature (e.g., the rods may be pre-bent) to mimic the curvature or lordosis of the spine. Alternatively, the rods may be substantially straight and/or may be bendable so that the surgeon can bend the rods prior to installation.

As will be appreciated by those skilled in the art, any or all of the components described herein such as, for example, the rods, damping components, housings, end caps, etc. may be provided in sets or kits so that the surgeon may select various combinations of components to perform a fixation procedure and create a fixation system which is configured specifically for the particular needs/anatomy of a patient. It should be noted that one or more of each component may be provided in a kit or set. In some kits or sets, the same device may be provided in different shapes and/or sizes (e.g., multiple rods, damping components, housings and/or end caps of different sizes).

While the foregoing description and drawings represent the preferred embodiments of the present invention, it will be understood that various additions, modifications, combinations and/or substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. In addition, features described herein may be used singularly or in combination with other features. The presently disclosed embodiments are therefore to be considered in all respects as illustrative and not restrictive, the scope of the invention being indicated by the appended claims, and not limited to the foregoing description.

What is claimed is:

1. A dynamic fixation system for stabilizing adjacent vertebrae, the system comprising: a first rod having a first end comprising a housing in the form of a cage, the cage comprising a plurality of holes dispersed around the housing's periphery and an inner cavity which can be accessed through any one of the plurality of holes; a second rod having an inner enlarged end and an outer enlarged end, wherein the inner diameter of the inner cavity of the housing is larger than the outer diameter of the inner enlarged end such that the inner enlarged end can be slidably received within the inner cavity and a gap is formed between the inner cavity and the entire outer circumference of the inner enlarged end, and the inner diameter of the inner cavity of the housing is larger than the outer diameter of the outer enlarged end such that the outer enlarged end can be slidably received within the inner cavity and a gap is formed between the inner cavity and the entire outer circumference of the outer enlarged end; and a damping component, wherein the damping component substantially fills the inner cavity of the cage, including filling in the gap between the inner cavity and the entire outer circumference of the inner enlarged end and filling in the gap between the inner cavity and the entire outer circumference of the outer enlarged end such that the inner enlarged end and the outer enlarged end are encapsulated within the housing by the damping component, and the damping component additionally occupies space around the periphery of the housing, and wherein the dynamic fixation system, once installed, enables attached adjacent vertebrae to move with respect to one another.

2. The dynamic fixation system of claim 1, wherein the damping component is injected molded into the housing via the plurality of holes.

3. The dynamic fixation system of claim 2, wherein the injected molded damping component cures and hardens in at least one of the plurality of holes.

4. The dynamic fixation system of claim 1, wherein the housing is integrally formed with the first rod.

5. The dynamic fixation system of claim 1, wherein the first and second ends are integrally formed with the first and second rods respectively.

6. The dynamic fixation system of claim 1, wherein the damping component is selected from one of a gel core, a hydrogel, a silicon, an elastomeric material, a rubber and a combination thereof.

7. The dynamic fixation system of claim 1, wherein the damping component is a polycarbonate urethane.

8. The dynamic fixation system of claim 1, wherein the inner enlarged end includes a plurality of openings so that the damping component can be injected into the housing through the openings.

9. The dynamic fixation system of claim 1, wherein the damping component is injected over and around the housing.

10. The dynamic fixation system of claim 1, wherein the damping component is injected into the housing via a passageway formed in at least one of the first and second rods.

11. The dynamic fixation system of claim 1, wherein the diameter of the inner enlarged end is equal to the diameter of the outer enlarged end.

12. The dynamic fixation system of claim 1, wherein the diameter of the inner enlarged end is greater than the diameter of the outer enlarged end.

13. The dynamic fixation system of claim 1, wherein the diameter of the inner enlarged end is smaller than the diameter of the outer enlarged end.

* * * * *